(12) United States Patent
Butz-Ostendorf et al.

(10) Patent No.: US 11,495,330 B2
(45) Date of Patent: Nov. 8, 2022

(54) NEUROLOGICAL DATA PROCESSING

(71) Applicant: Biomax Informatics AG, Planegg (DE)

(72) Inventors: Markus Butz-Ostendorf, Landsberg am Lech (DE); Sascha Losko, Munich (DE); Wenzel Kalus, Gauting (DE)

(73) Assignee: Biomax Informatics AG, Planegg (DE)

( * ) Notice: Subject to any disclaimer, the term of this patent is extended or adjusted under 35 U.S.C. 154(b) by 385 days.

(21) Appl. No.: 16/486,378

(22) PCT Filed: Feb. 15, 2018

(86) PCT No.: PCT/EP2018/053813
§ 371 (c)(1),
(2) Date: Aug. 15, 2019

(87) PCT Pub. No.: WO2018/149930
PCT Pub. Date: Aug. 23, 2018

(65) Prior Publication Data
US 2020/0005932 A1  Jan. 2, 2020

(30) Foreign Application Priority Data

Feb. 17, 2017  (GB) .................................. 1702600

(51) Int. Cl.
*G16H 30/40* (2018.01)
*G16B 50/10* (2019.01)
(Continued)

(52) U.S. Cl.
CPC ............ *G16B 50/10* (2019.02); *G16B 45/00* (2019.02); *G16B 50/00* (2019.02); *G16B 50/30* (2019.02); *G16H 30/40* (2018.01); *G16H 70/60* (2018.01)

(58) Field of Classification Search
CPC ........ G16B 50/10; G16B 45/00; G16B 50/00; G16B 50/30; G16H 30/40; G16H 70/60
See application file for complete search history.

(56) References Cited

U.S. PATENT DOCUMENTS

| 2018/0107793 A1* | 4/2018 | Ni ........................... G16H 10/60 |
| 2018/0253732 A1* | 9/2018 | Bakalash ............... G06Q 50/01 |

(Continued)

OTHER PUBLICATIONS

Losko et al. "Knowledge Networks of Biological and Medical Data: An Exhaustive and Flexible Solution to Model Life Science Domains" *Data Integration in the Life Science*, 232-239, Jan. 2006.
(Continued)

*Primary Examiner* — Reginald R Reyes
(74) *Attorney, Agent, or Firm* — Occhiuti & Rohlicek LLP

(57) ABSTRACT

The present invention is in the technical field of bioinformatics, and the implementation of bioinformatics. Advances in technology have led to a large increase in the rate at which data, in particular in the medical domain, can be generated (from patient sources, clinical trials, and research campaigns). The researcher is thus confronted with a large amount of information, and it is difficult to discover connections in the data, and thus to improve medical knowledge, even in spite of the amount of data available. The present application proposes to process and to structure medical data using a computer-implemented semantic network, enabling undiscovered connections between experiments and data sources to be made, and to continually add new data to the semantic network. In summary, it is proposed to provide a computer-implemented method and associated system which are able to automatically provide neurological knowledge model data by annotating neural connectivity data with further data sources.

14 Claims, 15 Drawing Sheets

(51) Int. Cl.
*G16H 70/60* (2018.01)
*G16B 45/00* (2019.01)
*G16B 50/00* (2019.01)
*G16B 50/30* (2019.01)

(56) References Cited

U.S. PATENT DOCUMENTS

2018/0368720 A1* 12/2018 Lee .................. G06T 7/0012
2019/0150742 A1* 5/2019 Lee .................. A61B 5/7253

OTHER PUBLICATIONS

Cano et al. "The COPD Knowledge Base: enabling data analysis and computational simulation in translational COPD research" *Journal of Translational Medicine, Biomed Central,* 12: S6, Nov. 2014.

Maier et al. "Knowledge management for Systems Biology a general and visually driven framework applied to translational medicine" *BMC Systems Biology,* 5: 38, Mar. 2011.

Maier et al. "The Bio XM Knowledge Management Environment: a general and visually driven framework applied to integration of large biological datasets" *BMC Systems Biology,* 38, Nov. 2014.

Taylor, Peter N. et al., "Within Brain Area Tractography Suggests Local Modularity Using High Resolution Connectomics," Scientific reports 7.1 (2017): 1-9.

Torgerson, Carinna M. et al., "DTI Tractography and White Matter Fiber Tract Characteristics in Euthymic Bipolar I Patients and Healthy Control Subjects," Brain Imaging Behav. 7(2): 129-139 (2013).

Losko, Sascha et al., Knowledge Networks of Biological and Medical Data: An Exhaustive and Flexible Solution to Model Life Science Domans, Data Integration in the Life Sciences pp. 232-239 (2006).

* cited by examiner

NEUROLOGICAL DATA PROCESSING

CROSS REFERENCE TO RELATED APPLICATIONS

This application is the national phase under 35 USC 371 of international Application No. PCT/EP2018/053813, filed Feb. 15, 2018, which claims priority to a British patent application 1702600.6 filed Feb. 17, 2017.

FIELD OF THE INVENTION

The present invention is in the general field of bioinformatics, and the implementation of bioinformatics. It concerns a computer-implemented neurological data processing method, an apparatus for processing neurological data, a computer program element and computer program product, and computer-implemented client-side and server-side neurological data processing methods.

BACKGROUND

Sources of data having relevance to medical applications, and in particular having relevance to brain science and neurology, come in many different forms. In the domain of neurology and brain science more generally, a brain scan of a patient has traditionally been made using a Computed Tomography (CT) scan, or a Magnetic Resonance Imaging (MRI) scan. Such scans have been able to reveal the bulk properties of the brain tissue of a patient at a region of interest of use for brain cancer diagnosis, or for post-stroke assessment, for example. Such scans have, however, on their own not been useful for more detailed investigations of brain function.

FIG. 1a) illustrates an example of a low-resolution 2D structural connectivity heat map (matrix) of a patient brain acquired from a Diffusion Tensor Imaging (DTI) scan. In this image, a location on the x-axis of the graph represents a first location in a vertebrate brain, and a location on the y-axis represents another location in the same vertebrate brain. The intensity of a data point in the heat map intersected by lines from the x and y axes represents the strength (thickness) of a structural connection (i.e. a neural fibre tract connecting the two locations) between those two points acquired by DTI. Of course, as the 3D coordinate points for each of the x and y axis data entries are usually known, it is possible to plot 3D "connectome" visualizations of a vertebrate brain from such data.

FIG. 1b) illustrates an example of a low-resolution 2D functional connectivity heat map (matrix) of a patient brain from a functional Magnetic Resonance Imaging (fMRI) scan. Whilst DTI focusses on the structural connectivity of the brain, an fMRI scan obtains information about the correlation in time and space between neural activity levels in different brain areas. Thus, an intensity of a data point in the heat map of FIG. 1b) intersected by lines from the x and y axes represents the strength of the functional correlation between various brain areas.

The data matrices of FIGS. 1a) and 1b) only show a fraction of the typical data matrices usually obtained.

Connectomics is a relatively new area of research focussing on an investigation of the strength of structural and or functional neural links between different regions of brain tissue. Connectomics has been made possible by these developments in brain imaging technology.

In brief, diffusion Tensor Imaging (DTI) is an MRI-based approach which exploits the fact that, when imaging a brain, water diffuses more rapidly in a direction associated with a direction aligned with an internal structure of a bundle of nerve fibres. Thus, computation of the diffusion tensor over a region of brain tissue can enable insights into the connectivity of that brain tissue to be found.

In brief, functional MRI (fMRI) is an imaging approach that has exploited the knowledge that the properties of oxygen-rich blood can be detected using an MRI scanner. In addition, it is known that brain haemodynamics is linked to neural activity. Active neurons demand more oxygenated blood, and displace deoxygenated blood. The haemoglobin in blood cells which carry oxygen is diamagnetic when oxygenated, but more paramagnetic when deoxygenated. This difference between deoxygenated and oxygenated blood causes a varying Magnetic Resonance signal, which can be mapped to discover which neurons are active at a time.

Thus, because fMRI and/or DTI information can provide information about neural connectivity and/or activity, this information can be applied, for example, to enhance neurology research, or for clinical medical applications.

The connectome is generally considered as a three-dimensional data construct comprising all available information about how all of the neural areas in a brain are connected to each other. Connectome information can be derived from measurements in a living human like DTI (structural connectome information) or fMRI, MEG, EEG (functional connectome information). Structural connectome information can also be obtained from post-mortem traces studies or high resolution polarized light imaging. The three-dimensional data of an individual brain can be mapped onto a normalized standard brain (for example, the MNI 152 template: http://www.bic.mni.mcgill.ca/ServicesAtlases/ICBM152NLin2009)

A specific example is discussed in US 201610284082A1. This document is in the field of surgical planning, and discusses a method of determining a "vulnerability field" of a patient's brain prior to surgery. A nerve-indicating dataset, sourced, for example, from a DTI image, determines areas of a brain with neuron-rich areas of grey-matter. A weight indicating a measure of the connectivity of a voxel to other voxels can be assigned to each voxel, thus forming a "vulnerability field". In brief, the document proposes to overlay various surgical incision trajectories over the vulnerability field, and to determine which surgical incision trajectory results in a path which would cause minimal disturbance in the vulnerability field. It is surmised that the surgical incision path causing the least disturbance to the grey-matter would also result in better neuro-clinical outcomes for the patient concerned.

Although the approach in US 201610284082A1 can improve surgical planning, it is noted that in the field of neurology, data processing is highly customized to the data model present in a specific application. If new information is suddenly presented, it might not be possible to integrate that information in a useful way into the approach discussed above.

The integration of new information into a data model is frustrated by many aspects. Firstly, the size of the data files handled in the field of neurology can be huge—a single brain scan can reach hundreds of gigabytes. Secondly, although a data file for a single patient may yield useful information, the integration of different scans for the same patient taken at different times, or a comparison of a scan for the patient to a database of scans made on many different patients could be much more useful for comparative analysis. Still further, brain scans can be compared to related information such as gene atlases, functional ontologies, brain atlases, receptor atlases, and the like. However, the use of existing approaches would require the custom generation and programming of new software tools for each specific new combination of information desired.

In short, there has been a "data explosion" in the field of neurology caused by an improvement in neurological data acquisition technology, and in databases comprising neurological information. However, the ability to order and to search this information in a simple and intuitive way lags far behind. This stifles curiosity-driven research (because coding an entirely new software application to analyze a combination of data which it is proposed may be useful, might never be done for cost reasons). It increases the costs for pharmacological research.

Therefore, an improved approach to the automatic acquisition, processing, structuring, and analysis of neurological data is required.

SUMMARY OF THE INVENTION

It would be advantageous to have an improved technique for neurological data processing.

The object of the present invention is solved by the subject-matter of the independent claims, wherein further embodiments are incorporated in the dependent claims.

Towards this end, there is provided according to a first aspect of the invention a computer-implemented neurological data processing method comprising:
a) acquiring first element data and second element data representing, respectively, attributes of a first location and a second location in a subject vertebrate brain;
b) acquiring neural connectivity data linking the first element data and the second element data, wherein the neural connectivity data comprises a representation of a functional and/or structural connection between the first location and the second location in the subject vertebrate brain, and wherein the first element data, second element data, and the neural connectivity data form a semantic network;
c) acquiring annotation data comprising object data;
d) mapping the annotation data to the neural connectivity data to thus generate neurological knowledge model data related to the subject vertebrate brain, wherein the neurological knowledge model data is a semantic network capable of being queried using a formal linguistic specification, wherein the formal linguistic specification is derived from the semantic network; and
e) outputting the neurological knowledge model data.

Advantageously, the above approach enables a variety of other medical data sources to be used to annotate the neural connections between locations in location in a subject vertebrate brain. It thus becomes possible to correlate neural connectivity with many other medical or pharmacological phenomena.

Optionally, the neural connectivity data is brain connectivity data.

Optionally, the computer-implemented neurological data processing method is a computer-implemented brain data processing method.

Optionally, a computer-implemented neurological data processing method is provided wherein the first and second element data, and the neural connectivity data each comprise (i) a type data field which are each optionally dynamically typed.

Advantageously, it is possible to allow the first and second element data, and the neural connectivity data, to be dynamically typed, enabling the set of object types in the data model to be extensible at run-time. In other words, new data sources may be added, to enable the semantic network to evolve over time.

Optionally, a computer-implemented neurological data processing method is provided, wherein the neural connectivity data comprises (i) a neural connectivity source data field and (ii) a neural connectivity target field, enabling the association of the neural connectivity data with a plurality of sets of element data, and wherein the neural connectivity data further comprises (iii) neural connectivity class data defining an allowed set of relation configurations between the plurality of sets of element data.

Optionally, the computer-implemented neurological data processing method is provided, wherein the annotation data comprises (i) attribute definition data comprising an attribute type.

Optionally, the computer-implemented neurological data processing method is provided, wherein the annotation and/or element data is experimental data.

Advantageously, information from real-life patient experiments can be matched to neural links in a sematic network.

Optionally, the computer-implemented neurological data processing method is provided, wherein the experimental data comprises functional Magnetic Resonance Imaging (fMRI) data.

Advantageously, information about brain activity can be incorporated into the semantic model.

Optionally, the computer-implemented neurological data processing method is provided, wherein the experimental data comprises Diffusion Tensor Imaging (DTI) data.

Advantageously, information about the structural and/or functional aspects of brain connectomes can be incorporated into the semantic model.

Optionally, the computer-implemented neurological data processing method is provided, wherein the experimental data comprises Magnetic Encephalography (MEG) data.

Advantageously, functional information from MEG can be used to supplement the semantic network.

Optionally, the computer-implemented neurological data processing method is provided, wherein the experimental data comprises Positron Emission Tomography (PET) data.

Advantageously, it is possible to provide more accurate imaging data concerning, for example, receptor or tumour activity in the semantic network.

Optionally, the computer-implemented neurological data processing method is provided, wherein the experimental data comprises Single Photon Emission Computerized Tomography (SPECT) data.

Optionally, the computer-implemented neurological data processing method is provided, wherein the experimental data comprises data from a plurality of different patients.

Advantageously, data from a large number of patient clinical trials may be structured and organized independently.

Optionally, the computer-implemented neurological data processing is provided, further comprising:
a1) acquiring, as the first element data and/or the second element data, a brain structure coordinate defining a point in 3D space at which the experimental data has been acquired.

Advantageously, phenomena may be localized in the brain of a subject or patient.

Optionally, the computer-implemented neurological data processing method is provided, further comprising:

a2) acquiring, as the first element data and/or the second element data, brain parcellation data defining a brain region in 3D space at which the experimental data related to a brain region has been acquired.

Advantageously, it is possible to select a large "bundle" of neural connectivity data rather than having to input brain parcellation regions by manually annotating a large number of fibres.

Optionally, the computer-implemented neurological data processing method is provided, wherein in step c), the annotation data comprises anatomical brain atlas data.

Advantageously, neural connectivity data in the brain may be automatically related to its anatomical location.

Optionally, the computer-implemented neurological data processing method according to any preceding claim, wherein in step c), the annotation data comprises a gene expression atlas of a vertebrate brain ontology.

Advantageously, neural connectivity data in the brain may be automatically related to a gene expressed in both the origin and target region.

Optionally, the computer-implemented neurological data processing method is provided, wherein in step c), the annotation data comprises ontological brain atlas data.

Optionally, the computer-implemented neurological data processing method is provided, wherein in step c), the annotation data comprises a functional neurological model of a vertebrate brain.

Advantageously, neural connectivity data in the brain may be automatically related to the function of a particular brain region.

Optionally, the computer-implemented neurological data processing method according to one of the preceding claims, further comprising:

f) acquiring query data encoding linguistic descriptors of primitives in the element data from a user.

g) mapping the query data onto one or more items of element data in the neurological knowledge model; and h) generating query result data based on the mapping of the query data onto one or more items of element data in the neurological knowledge model data using the formal linguistic specification derived from the semantic network.

Advantageously, it is possible to search an entire semantic knowledge model with a natural language query, to quickly obtain new information from it.

Optionally, the first element data and/or the second element data represent location attributes of a first location and a second location, respectively.

Advantageously, the first element data and/or the second element data may be used to localize a feature such as the end of a fibre bundle or a receptor location in a vertebrate brain, or in data representing it.

Optionally, the computer-implemented neurological data processing method is provided, further comprising:

i) outputting the query result data.

Advantageously, the user can easily and quickly obtain a result of a medical query.

According to a second aspect of the invention, there is provided an apparatus for processing neurological data comprising:

a data input module;
an object data processing module;
a relationship data processing module;
an annotation data processing module; and
a data output module.

The object data processing module is configured to acquire first element data and second element data representing, respectively, attributes of a first location and a second location of a subject vertebrate brain.

The relationship data processing module is configured to acquire neural connectivity data linking the first element data and the second element data, wherein the neural connectivity data comprises a representation of a functional and/or structural connection between the first region and the second region of the subject vertebrate brain, and wherein the first element data, second element data, and the neural connectivity data form a semantic network.

The annotation data processing module is configured to acquire annotation data comprising object data, and to map the annotation data to the neural connectivity data to thus generate neurological knowledge model data related to the subject vertebrate brain, wherein the neurological knowledge model data is a semantic network capable of being queried using a formal linguistic specification, wherein the formal linguistic specification is derived from the semantic network.

The data output module is configured to output the neurological knowledge model data.

Optionally, the apparatus of the second aspect is provided, wherein the first and second element data each comprise (i) a type data field which are each optionally dynamically typed.

Optionally, the apparatus of the second aspect is provided, wherein the neural connectivity data comprises (i) an neural connectivity source data field and (ii) a neural connectivity target field, enabling the association of the neural connectivity data with a plurality of sets of element data, and wherein the neural connectivity data further comprises (iii) neural connectivity class data defining an allowed set of relation configurations between the plurality of sets of element data.

Optionally, the apparatus of the second aspect is provided, wherein the annotation data comprises (i) attribute definition data comprising an attribute type.

Optionally, the apparatus of the second aspect is provided, wherein the annotation data is experimental data.

Optionally, the apparatus of the second aspect is provided, wherein the data input module is configured to acquire functional Magnetic Resonance Imaging data (fMRI); and the experimental data comprises functional Magnetic Resonance Imaging data.

Optionally, the apparatus of the second aspect is provided, wherein the data input module is configured to acquire Diffusion Tensor Imaging data (DTI); and wherein the experimental data comprises Diffusion Tensor Imaging data.

Optionally, the apparatus of the second aspect is provided, wherein the data input module is configured to acquire Magnetic Encephalography (MEG) data; and wherein the experimental data comprises Magnetic Encephalography (MEG) data.

Optionally, the apparatus of the second aspect is provided, wherein the data input module is configured to acquire Positron Emission Tomography (PET) data; and wherein the experimental data comprises Positron Emission Tomography (PET) data.

Optionally, the apparatus of the second aspect is provided, wherein the data input module is configured to acquire Single Photon Emission Computerized Tomography (SPECT) data; and wherein the experimental data comprises Single Photon Emission Computerized Tomography (SPECT) data.

Optionally, the apparatus of the second aspect is provided, wherein the experimental data comprises data from a plurality of different patients.

Optionally, the apparatus of the second aspect is provided, wherein the data input module is further configured to acquire, as the first element data and/or the second element data, a brain structure coordinate defining a point in 3D space at which the experimental data has been acquired.

Optionally, the apparatus of the second aspect is provided, wherein the data input unit is further configured to acquire brain parcellation data defining a brain region in 3D space at which the experimental data has been acquired; and wherein the relationship data processing module is further configured to create a relation between the parcellation data and the first element data and/or the second element data.

Optionally, the apparatus of the second aspect is provided, wherein the data input unit is further configured to acquire brain anatomical brain atlas data; and wherein the annotation data processing module is further configured to map the anatomical brain atlas data to the relation data.

Optionally, the apparatus of the second aspect is provided, wherein the data input unit is further configured to acquire gene expression atlas data of a vertebrate brain; and wherein the annotation data processing module is further configured to map the gene expression atlas data to the relation data.

Optionally, the apparatus of the second aspect is provided, wherein the data input unit is further configured to acquire a functional neurological model of a vertebrate brain; and wherein the annotation data processing module is further configured to map the functional neurological model data to the neural connectivity data.

Optionally, the apparatus of the second aspect is provided, further comprising:

a query module.

The data input unit is further configured to acquire query data from a user.

The query module data processing module is further configured to map the query data onto one or more items of element data in the neurological knowledge model data, the entries in the query data encoding linguistic descriptors of primitives in the element data; and to generate query result data based on the mapping of the query data onto one or more items of element data in the neurological knowledge model data using the formal linguistic specification derived from the semantic network; and the data output module is configured to output the query result data.

According to a third aspect, there is provided a computer program element comprising instructions which, when executed by a computer, enables the computer to carry out the method of the first aspect or its embodiments.

According to a fourth aspect, there is provided a computer program product, tangibly embodied on a carrier medium, comprising software code for carrying out the method of the first aspect.

According to the fifth aspect, there is provided a computer program product, tangibly embodied on a carrier medium, comprising a data structure containing a neurological knowledge model generated according to the method of the first aspect.

According to a sixth aspect, there is provided a computer-implemented client-side neurological data processing method comprising:

p) receiving neurological query data from a user;
q) transmitting the neurological query data to a server-side neurological data processor, wherein the server-side neurological data processor comprises neurological knowledge model data generated according to the method of one of claims 1 to 19.
r) receiving query result data from the server-side neurological data processor;
t) displaying the query result data to a user.

According to a seventh aspect, there is provided a computer-implemented server-side neurological data processing method comprising:

u) receiving neurological query data from a client-side neurological data processor;
v) mapping the neurological query data onto one or more items of element data in neurological knowledge model data generated according to the method of one of claims 1 to 19, the entries in the query data encoding linguistic descriptors of primitives in the element data; and generating neurological query result data based on the mapping of the query data onto one or more items of element data in the neurological knowledge model data; and
w) transmitting the neurological query result data to the client-side neurological data processor.

Accordingly, it is a basic idea of the invention to enable a link in neurological data representing a structural and/or functional link in a connectome to be annotated with a wide range of other relevant external data. The structured data output resulting from such a process enables clinical or research insights about a patient to be more quickly discovered. An important difference between the semantic approach to the neural data in the present invention, and the prior art discussed above, is that in the approach of US 2016/0284082 A1, the application is "hard-coded" for the specific surgical resection application. In the case of the present technique, neural data is loaded into a flexible semantic network (implemented as a relational database) which can easily change as new information is constantly provided, in a way which is easy for a user to query.

DETAILED DESCRIPTION OF EMBODIMENTS

Figure 1A:
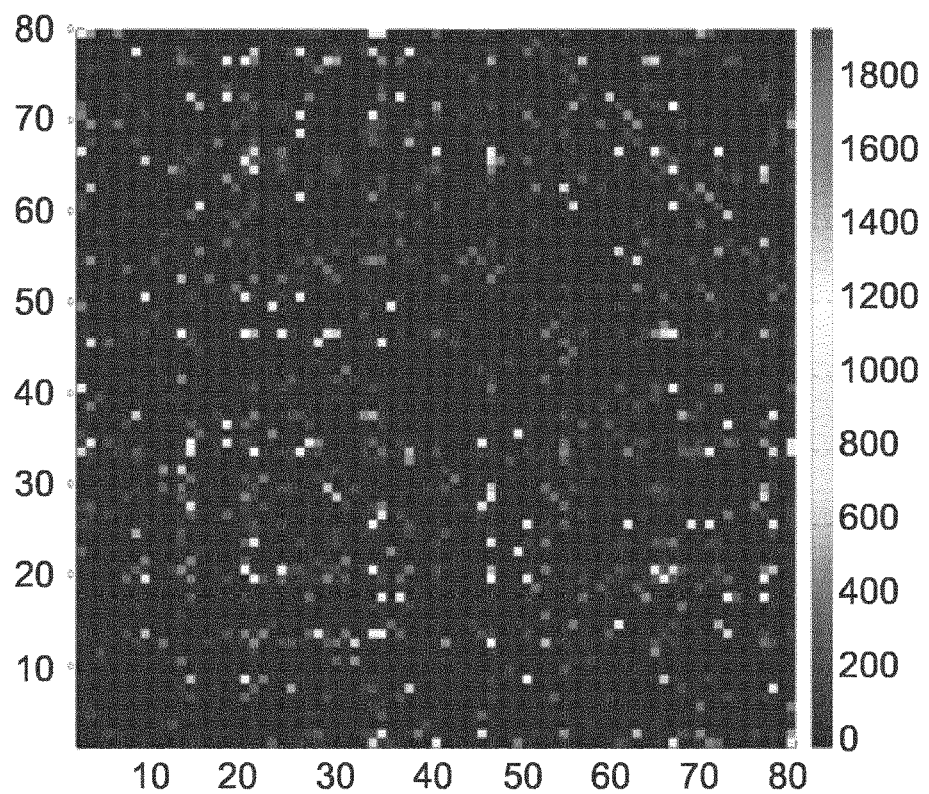
FIG. 1a) illustrates an example of a low-resolution 2D structural connectivity matrix of a patient brain acquired from a Diffusion Tensor Imaging (DTI) scan.

Life sciences research by academic and industrial research groups generates a large amount of new information every year, reflected in a growing body of scientific literature, and also a large body of formalized data, including experimental data. The following description presents a generic knowledge management environment with an ability to represent implicit and explicit knowledge, and to thus discover new knowledge between large bodies of previously existing data.

BioXM is a knowledge management tool aimed at life-sciences researchers, providing one solution to the increasing amount of data in the life-sciences field.

In the proposed system, it is proposed to order neuro-biological research based on the idea of connectomics, and enable the annotation of connectomic information with other sources of information. This is facilitated through the representation of knowledge data as a typed data relationship between semantic data objects representing "elements of a scientific domain", such as genes, or drugs. Annotation of such elements of a scientific domain with additional information can expand the knowledge network. Specific parts of the knowledge model may be organised in a sub-network context to allow a hierarchical structuring of knowledge.

In general, it is proposed that the identification of a distinct neural relationship (a fibre physical fibre bundle or a functional association in time) in a neurological image of a patient can be identified, showing a link between at least two brain areas, for example in absolute 3D space, or alternatively between parcellated brain areas. This link can be associated to a multitude of other data sources by annotating it with further object information, in the sense of the neurological data processing approach to be discussed herein.

Although structural and functional connectivity are certainly related, they are not identical. A strong structural connection can have an inhibitory effect on the connected brain area, causing the functional connectivity to be weakly or even anti-correlated, for example. Therefore, it is crucial to compare both structural and functional connectivity information.

Importance of Semantic Networks for Brain Connectome Analysis

The assessment of brain connectome analysis is becoming more important for diagnosis, pathophysiology, and the treatment of neurological and psychiatric diseases. Graph theoretical approaches have been the standard approach to assess human brain connectomes. However, graph-theoretical measures describe attributes of the network as a whole, but ignore the significance of individual connections inside the patient's connectome.

The cause of brain diseases can, in many cases, be attributed to alterations in specific connections (Bartolomeo P, Thiebaut de Schotten M, Doricchi F, "Left unilateral neglect as a disconnection syndrome", J. Cereb Cortex. 2007 November; 17(11):2479-90. Epub 2007 Jan. 31).

However, available tools provide little support for a connection-based analysis of brain information. It is proposed to apply the semantic network approach of the BioXM system to organize, to integrate, and to query connectome datasets derived from fMRI and/or DTI imaging, as the new "NeuroXM" platform. It has been found that such semantic network approaches beneficially enable a new, integrated analysis of patient connectomes, and thus a better understanding of brain disorders can be reached.

As a brief example addressed by the computer implementation of a neurology model to be discussed subsequently, an unsolved problem in the domain of neurology concerns the annotation of patients' neuroimaging datasets with external, publicly available meta-information. One example of such meta-information would be functional brain atlases, in order to group and select brain areas and connections by anatomical systems and subsystems or functional domains. The easy linkage of a patient's fMRI scan with a classification of functional behaviour, such as the Brede ontology (http://neuro.compute.dtu.dk/wiki/Main_Page) would enable the user to select those brain areas and connections which are for example associated with the emotions of pleasantness or anger.

The "Brede ontology" is a database containing data entries with an assessment of the functional behaviour of the human brain with relevant brain areas involved in the respective cognitive task. These behavioural changes are increasingly thought to be a function of the layout of connectivity between points in the brain (connectome). It would be advantageous to be able to select relevant connections associated with a particular cognitive function as annotated by the Brede ontology and compare differences in the neural connection pathways in a patient with those of a control subject, enabling experimental control information to be integrated from public sources such as the Human Connectome Project (http://umcd.humanconnectomeproject.org/).

Of course, the patient's fMRI scan results will evolve over time, as research results are generated and as the patient heals. The BioXM approach enables approach easy integration of the large amount of information thus generated into a data model, giving an easy comparison between different fMRI scans at multiple time points, or perhaps the scans of other control patients, would enable better patient treatment outcomes and also could lead to new research results. In other words, a significant amount of useful data exists for the purpose of neurology research, but there it is a challenge to order and establish relations between such large quantities of such data to make it more useful.

This description now proceeds with a high-level discussion of knowledge models, as implemented using the BioXM platform provided by Biomax Informatics AG, Planegg, Germany. Then, the module arrangement of the new NeuroXM platform of the BioXM system is discussed, as it applies to the computer implementation of a neurology model. Then, examples and embodiments of the invention are discussed, and real-life application cases are provided.

Introduction to Knowledge Models

The proposed solution to the problem of data overflow in neurology is the integration of objects through public and proprietary databases (in the area of neurology, and others) into a relational database management system (RDBMS) so that these databases can serve as "virtual semantic objects". In the present approach, all semantic objects (as will be discussed, these number at least "elements", "relations", "contexts", "ontology instances", or "external database entries") can be annotated with additional information.

The knowledge model thus built can be browsed through graphically, using a GUI. Alternatively, a query builder enables complex queries to be formed, using a natural-language like syntax, which is based on the particular arrangement of semantic objects in the knowledge model.

Semantic network definitions combine the requirements (a) to formulate a descriptive model of the knowledge environment in a particular area (the "world"), and (b) enable data resources to be related to that model. The approach to be discussed in this application enables the extension of the knowledge model, and its semantic, to evolve during run-time in a systematic way, like a model made of "LEGO®" building blocks. By combining new objects, the knowledge model (and its semantic) evolves. For example, a simple model to be used by a clinician could involve comparing fMRI results of a recovering brain trauma patient with a static instance of the Brede functional ontology. As successive new fMRI results for the patient are loaded into the knowledge model, the model is enriched with information about how the brain healing process could affect the patient's functional behaviour.

The present Applicants have discussed previous work associated with the basics of knowledge models in the article "Semantic data integration and knowledge management to represent biological network associations", by Losko S, Neumann K, Methods Mol Biol. 2009; 563:241-58. doi: 10.1007/978-1-60761-175-2_13, PM ID: 19597789"

Semantic Object (i)—"Element"

The element is the basic unit of a knowledge model. For example, a "GENE" element can be used to create the "STAT3" gene element, or the "Disease" element type can be used to create the "pancreatic tumour" disease element in the knowledge model. Elements thus form the generic nodes in a knowledge model (graph). It is a basic principle that each instance of an element should reflect exactly one unique real-world object.

Semantic object (ii)—"Relation"

The relation describes a relationship between semantic objects. Relations are, thus, "edges" in a knowledge model (graph). Relations are directed, and typed in terms of which objects they are allowed to connect to. For example, the "Gene-disease" relation class can be used to create the relation "STAT3 is associated with pancreatic cancer".

Semantic object (iii)—"Annotation"

The annotation extends the properties of a semantic object by a set of attributes. Thus, annotations allow supplementary information to be assigned to a semantic object and managed by the knowledge model. Annotations can be viewed as "data about data", to describe the annotated object with various data from external sources. For example, the semantic object can be extended by a gene report, a patient report, a protein entry, a literature abstract, or experimentally acquired data. An annotation does not need to be assigned only to one semantic object—in fact, it can be shared with multiple semantic objects. Optionally, an annotation can consist of multiple, hierarchically organized annotations constituting a data structure.

Semantic object (iv)—Ontology

The ontology classifies semantic objects according to a defined hierarchical nomenclature of concepts. The ontology is the link between the semantic network comprising the semantic objects, and knowledge management. Relations within an ontology are typically defined using a formal semantic, for example: "A is part of B" (meronymy), "A is a B" (hyperonomy) or "A is the same as B" (synonymy). This allows rule-based inference based on the ontology. The present computer-implemented neurological data processing approach allows any relation type, supporting transitive and reflexive relation types. Ontologies are often developed by domain experts as a set of "scientific nomenclature", and these are widely used in the life sciences. Thus, for example, gene ontologies are available to classify biological function. The NCI thesaurus of disease terms has classified diseases.

Semantic object (v)—Context

A set of semantic objects is a context. For example, metabolic pathways, protein complexes, and disease processes or patterns could all be considered to be a context. Thus, contexts enable the representation of different levels of abstraction, and may be thought of as sub-networks.

Queries

Queries are generated based on the structure of the knowledge model. Everything that is described in the model can be an argument in a query expression. Any change to the knowledge model has an effect on the queries that may be formulated. For example, the "Human Allen Brain Atlas" http://human.brain-map.org/provides microarray data containing gene expression data present in the human brain. Importing the Human Allen Brain Atlas into a semantic network containing a patient fMRI experiment, and the Brede ontology, effectively would extend the knowledge model and permit queries isolating an individual brain connection, gene expression, and functional behaviour.

Information Layers

An information layer enables semantic objects to be organized according to complexity (whereas a context organizes according to meaning). For example, a metabolic pathway may constitute a context. Proteins and metabolites can be defined as a layer that establishes the general picture. Side reactions can be defined as a second layer, flux in the network as a third information layer, and so on.

Graphs

A graph is used to visualize a semantic object with its associated objects, and thus is often used in GUIs. A graph can be used to navigate and explore the knowledge model, and also to formulate questions, such as "are there connections between any given node in the graph".

Experimental Data

Experimental data may be thought of as a special type of annotation—of samples or measurements taken from a patient. Thus, patient connectomes obtained via an fMRI scan (and/or a DTI scan) fall into this category. In the present invention, experiments are given a special identity because they often involve large datasets, interaction with external analytical tools, and the like. Thus, experiment objects represent a design pattern for high-throughput experiments.

Technical Architecture of a Neurology Model

Having discussed the high-level attributes of a knowledge model, the implementation of the technical architecture and object model of a computer-implemented neurological data processing method according to the present invention will be discussed.

Figure 2:
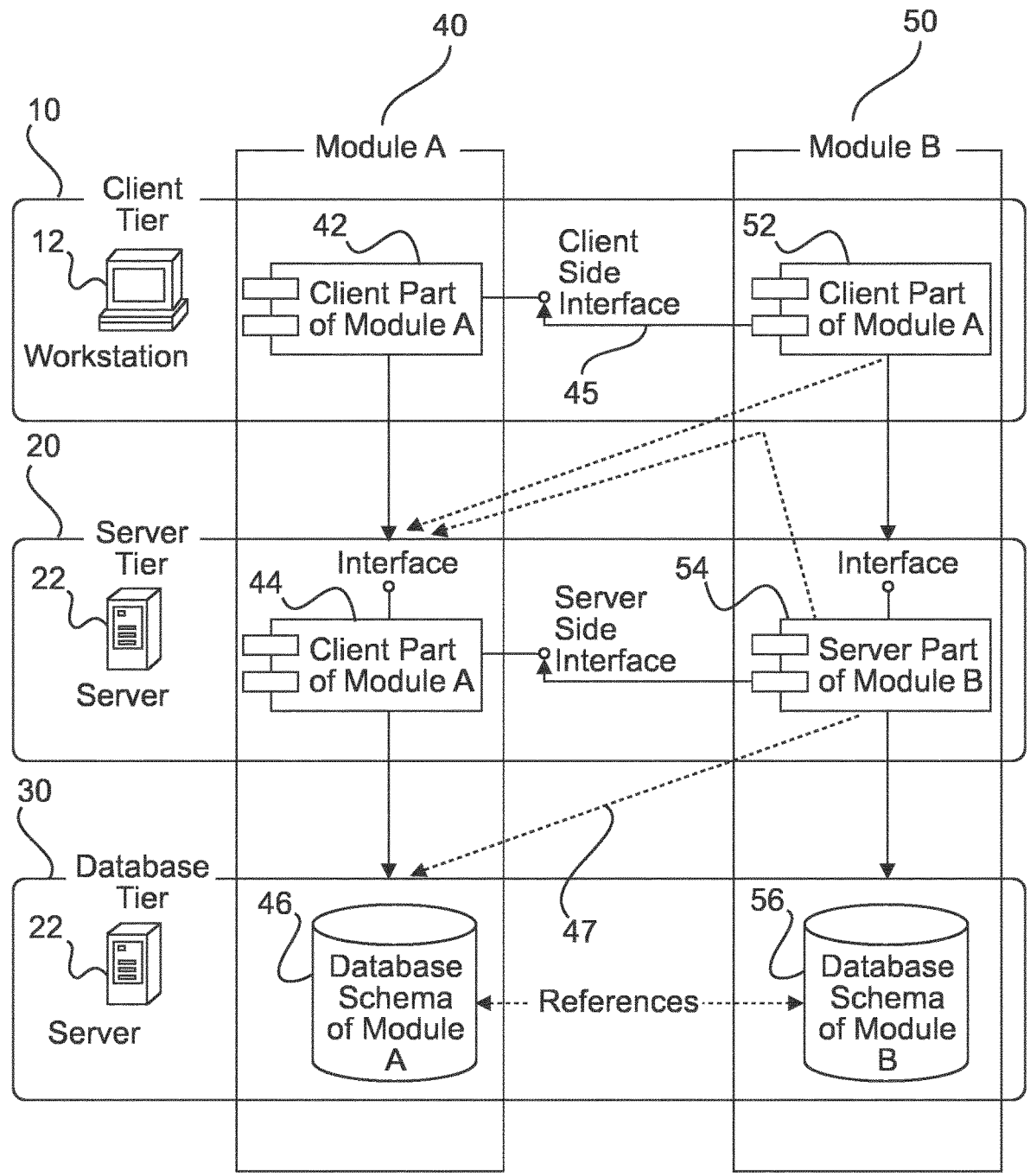
FIG. 2 illustrates a network of tiers and modules in an exemplary computer-implemented neurological data processing system.

FIG. 2 illustrates a client, database, and server tier of a computer-implemented neurology model.

The system comprises a set of three tiers—the client tier 10, the database tier 20, and the server tier 30.

The client tier 10 comprises one, or a plurality, of clients 12 communicating with the server 22. Optionally, the clients communicate with the server using the "Internet Inter-ORB" (IIOP) protocol. IIOP is a part of the Common Object Broker Request Architecture (CORBA). Generally, IIOP enables distributed software to be written and operated, guaranteeing that the distributed elements of the software are available using only a service designator and a program name, without having to understand other specifics about the system that the distributed programs are executing on.

The client tier 10 of the computer-implemented neurology model is configured to perform user interaction functions. Optionally, the client tier may be configured to perform functionality specific to the client and its implementation technology, or functionality which should be performed at the client side for performance or security reasons. For example, high-speed searching of experimental databases located at the client side would, in an embodiment, be performed at the client side. The client tier 10 also establishes the persistency of the client tier's configuration which are specific to the location or environment of the client tier 10, and for which local storage is a reasonable approach. Thus, local user preferences are, in an embodiment, stored at the client tier 10.

Optionally, the client tier 10 may be embodied on the client terminal 12 as a "SWING" GUI, Java® "Servlets", or a command line interface.

The server tier 20 primarily includes an implementation of all public Java(®) databases used by the clients 12 in the client tier 10. The server tier 20 manages persistency with the database tier 30. The client tier 10 does not automatically interact with the database tier 30. The server tier implements "business logic", which is that functionality which is not specific to the implementation technology of a particular client 12, and which may be implemented in the server tier 20 without a detrimental effect on performance. The server tier 20 is also tasked with maintaining the constraints of the data model and invariants. Exposed Java® interfaces and their implementation ensure that it is not possible to turn the database into an inconsistent state. The server tier 20 handles the basic security tasks of user authentication and authorization. According to an embodiment, exposed Java® interfaces and their implementation ensure that no client bypasses the system's security rules. Optionally, the server tier 20 is responsible for the logging of user actions—the exposed Java® interfaces mean that no client can bypass the audit rules. Optionally, the server tier 20 is responsible for interacting with external services. Examples of such external interfaces, such as brain atlases or large external repositories of clinical experimental data.

The database tier 30 comprises a relational database management system (RDBMS) instance used by a database server 32. This functions to ensure the persistence of all data. The RDBMS may take many forms, but should preferably support transactions and, provide a Java® database connectivity driver. The RDBMS preferably be supported by "Hibernate®", (http://hibernate.org/), a domain model for enabling persistence in relational databases. Preferably, the database 32 is implemented using "MySQL" ®, "Maria DB" ®, or "Oracle(®) RDBMS", although many other types of RDBMS database systems could be used.

Modules

FIG. 2 illustrates Module A 40 and Module B 50, overlaid onto the client tier 10, the server tier 20, and the database tier 30. The computer implementation of the neurology model is based on a set of modules which are responsible for encapsulation of system functionality (or certain aspects of the system's functionality). In general, a module may cross all tiers of the system. Optionally, some modules may provide functionality only to one tier, or several tiers. When designing the system, the decomposition into modules is based on the database design concepts of responsibility, dependence, and coupling. Ideally, a module should have clear responsibilities, contain highly coupled functionality, and be loosely coupled with the functionality provided by the other modules.

Figure 1B:
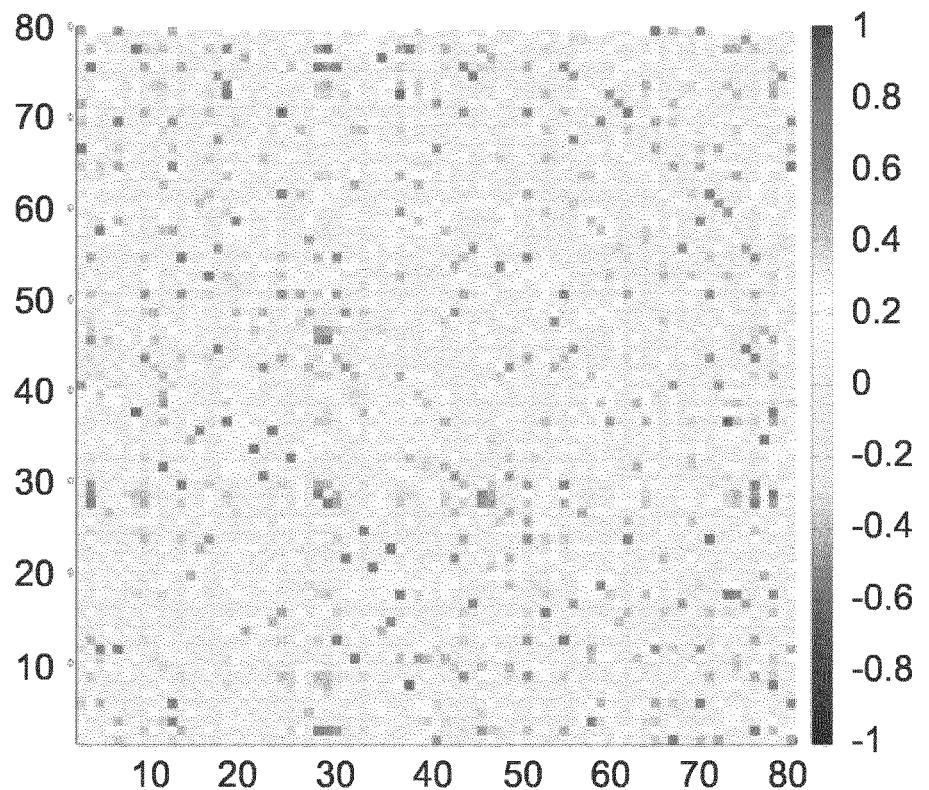
FIG. 1b) illustrates an example of a low-resolution 2D functional connectivity matrix of a patient brain from a functional Magnetic Resonance Imaging (fMRI) scan.

According to the representation of FIG. 1, a typical module has a client part 42, a server part 44, and a database part 46. Each module may depend on other modules, although circular dependencies are ideally to be avoided. Optionally, all module dependency rules in the database dependency rules are transitive. "if Module A 40 is allowed to depend on Module B 50, and if Module B 50 is allowed to depend on Module C, then Module A 40 is also allowed to depended on Module C".

The client part 42 of Module A uses and depends only on interfaces exposed to the client tier 10 by the server part 44 of Module A 40, interfaces exposed to the client tier 10 by the server parts 54 of other modules such as Module B 50, and client-side interfaces exposed by the client parts of other modules (for example, Module B 52). Optionally, the client part 42 of a module may provide client side interfaces 45 exposed to other modules.

The server part 44 of Module A 40 uses and depends only on the database part 46 of Module A 40, database schema fragments exposed by the database parts 56 of other modules, and server-side interfaces 47 exposed by the server parts of other modules, like Module B 50. Optionally, the server part 46 of a module, such as Module A 40, may provide at least an interface exposed to the client tier 10, and server-side interfaces exposed to other modules.

The database part 46 of Module A 40 provides a fragment specific to Module A 40 of the overall database schema. To provide good encapsulation, the database schema of Module A 40 is not connected with the database schema of Module B 50, or other modules (via RDBMS, foreign keys, or Hibernate® object references). Preferably then, the database schema of the database part 46 of Module A 40 is only used with the server part 44 of Module A 40.

Optionally, direct cross references between fragments of the database schema belonging to different modules may be allowed, enabling cross-module access to the database schema. Although such cross-module access is generally undesirable, it may be that for reasons of performance, data integrity, or simplicity, this general rule can be relaxed in specific cases. Whether, or not, the database schema of the module is exposed to other modules (and which parts) is defined on a per-module basis.

FIG. 2 illustrates how generic modules form the framework for the implementation of other modules. In general, the degree of genericity between modules may differ. There is a flexible separation between generic (framework) and non-generic (application) modules. An artificial separation does not need to be enforced by technical means, enabling the construction of a very flexible and extensible knowledge model.

The behaviour of the knowledge model discussed previously is implemented in the database system described above using a series of modules. Modules used to implement the neurological data processing system are now discussed.

Framework Module

The framework module is the system "kernel", providing a basic technical infrastructure to be used by other modules. The module includes (i) a server process implementation, (ii) a framework for server-side "plugins", (iii) a framework for data persistency and database access, (iv) a framework for checking references between database entities and cascade deletion, (v) a framework for client-server interaction and transactions, (vi) a framework for Swing® GUI applications and generic GUI components, (vii) a framework for long-running GUI tasks and background GUI tasks, (viii) support for asynchronous cancellation of long-running server calls, and (ix) Java(®) "web-start" support. In addition, the framework module optionally hosts routines for working with XML, files, buffers, the IIOP interface protocol, command line options, encryption, text-list based generic URLs, UUIDs, text pattern expressions, and performance benchmarking. The framework module may thus be thought of as the host, or "operating system" of the knowledge management system.

Object Module

Semantic objects (i) to (v) briefly outlined above are considered first-line objects, and the object module hosts and provides a framework for handling these objects. All other modules operating on first-class objects are built on this module.

The module optionally includes at least one of the items from the following list (i) a framework for static types, dynamic types, and first-class objects, including support for transient objects, (ii) a framework for basic object properties (name, description), (iii) a framework for audit object properties, (iv) a framework for GUI properties for objects and object types, (v) a framework for object-type extensions, (vi) a framework for object scopes and scope-capable objects, (vii) a framework for object deletion, (viii) a framework for exporting XML lists, (ix) a framework for variable handling, (x) a framework for external program parameters, and (xi) various generic GUI components for working with objects.

Relation Module

The module "relation" provides a generic facility for both relations and context management. Relations connect elements, and this module provides the ability for the definition of different relation classes, to create relations connecting arbitrary pairs of relation capable objects, to handle relations as first-class objects, and to use relations in search, reporting, and various other operations.

The module further enables the definition of different context classes, the creation of contexts comprised of arbitrary sets of context-capable objects, and relations between these objects, to handle contexts as first-class objects, and to use contexts in search, reporting, and various other operations.

The module includes one or more of (i) a sub-module enabling data-management of relation classes and relations, (ii) a sub-module enabling data-management of context classes and contexts, (iii) a sub-module enabling the instantiation of a relation as a first-class object, and (iv) a sub-module enabling instantiation of context as a first class object.

Annotation Module

The annotation module provides a generic module for annotation. The module enables different forms of annotation to be generated, each having its own set of annotation attributes of various supported annotation attribute types. Instances of these annotation forms, called "annotations", can be generated by filling annotation attribute values, assigning annotations to arbitrary annotation-capable objects, using annotations in search and reporting, and handling annotations as first-class objects.

The Annotation module includes (i) a framework for annotation attribute types, and a collection of different attribute types, (ii) a framework for annotation-capable objects, (iii) data management for annotation forms, annotation attribute definitions, annotations, annotation attribute values, annotation form-to object type, and annotation to object assignments, (iv) annotation as a first-class object, (v) full-text indexing functionality for "text document" annotation attribute types, (vi) a framework for annotation of numerical data associated with a physical unit, supporting implicit transformation between units, and (vii) a functionality of automatic generation of global views for all existing annotation forms.

Ontology Module

This module provides a generic module for ontology management. Thus, different ontologies can be imported from various supported ontology formats. Ontology entries and ontology relations can be handled as first-class objects. The module includes the ability to handle ontology data, a framework and support for importing various ontology formats, and ontology entry and ontology relation as first-class object.

Search Module

This module implements a generic search facility. This provides the ability to construct complex search queries consisting of an arbitrary set of various search criteria, possibly interconnected with each other in complex ways. These queries can be used to search for first-class objects, work with the resulting object sets, and to perform operations based on a query concept.

The module includes (i) a framework for search criteria, (ii) a collection of generic search criteria, (iii) a framework for query execution, including support for combining query parts having a completely different execution mechanism (RDBMS, external applications) into a single query in a unified way, support for using JOIN, sub-query, and temptable strategies for SQL based parts, support for execution plan analysis and user-defined hinting, support for the AND, OR, NOT operators, (iv) a query-builder GUI framework, (v) data management of query-objects and query templates, (vi) Query object as a first class object, (vii) GUI-side support for working with queries and query templates, (viii) a framework for quick-search in object lists, and (ix) a support for report-based server-side sorting in object lists.

Aspects of the BioXM Objects and Types framework relevant for providing the neurological data processing method and apparatus discussed herein are now discussed.

Objects/Types framework

These concepts are intended to provide the model and the framework for working with objects of various types (and objects representing the types of these objects) in a generic way. This supports the implementation of the generic services, which may thus be decoupled from the concrete entities of the application data model, providing their functionality for objects of different types.

Figure 3:
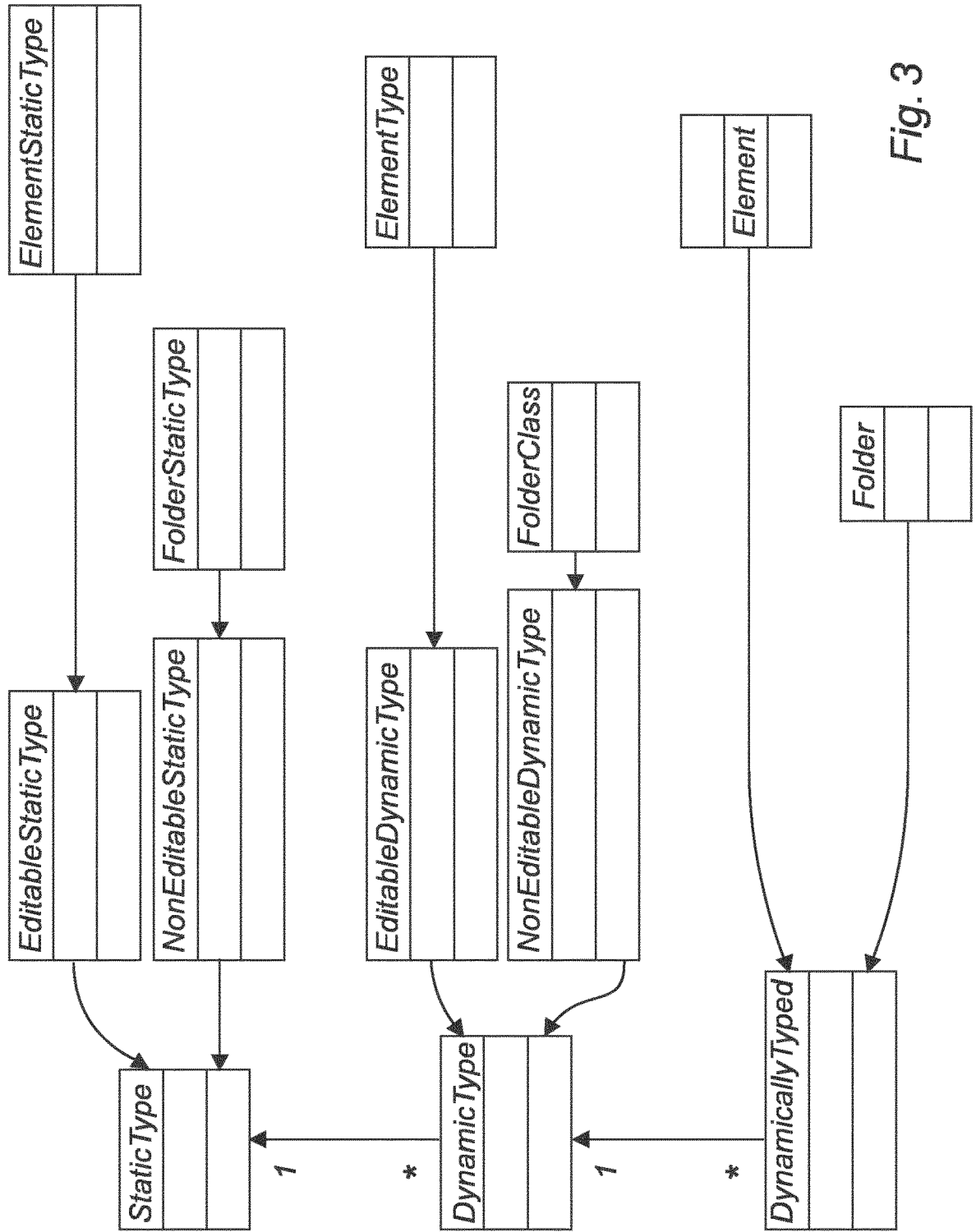
FIG. 3 illustrates an example of the BioXM object-type framework.

FIG. 3 illustrates the BioXM Object/type framework.

Dynamically Typed Object

Dynamically typed objects comprise a static type defined at application design-time, and their dynamic type, which is defined in run time. For example, a dynamically typed object relevant to a block of fMRI imaging data might be defined with a number of static type fields native to a particular fMRI scanning format. The fMRI imaging data would be dynamically typed in the sense that it could be dimensioned to be larger or smaller, dependent on the scan output. This allows the set of object types supported by the application to be rub-time extensible. Optionally, users may define their own object types. For example, in this model, "brain structures" are dynamically typed objects of the dynamic type "brain structure" (of static type "element"). In most cases in this specification, when the term "Object" is used, it is usually assumed that the term "dynamically typed object" is intended.

Thus, a "dynamic type" is an object type which is defined at run-time, and may not be known at design time. Each "dynamic type" belongs to a specific" static type", and logically represents the subtype of this "static type": Each "dynamic type" has a name unique to its static type. For example, the object type "brain structure" is a dynamic type of the static type "element".

Static Type

A static type is an object type which is defined at design-time (otherwise known as "object kind"). The static type represents a family of dynamic types. The exact set of dynamic types belonging to a dynamic type is, in general, not known at design-time and is defined at run-time. Different static types may support different degrees of flexibility of configuration of the set of dynamic types, for the same static types.

As an exemplary hierarchy of "static types" and "dynamic types" for a neurobiological data processing application, Table 1 may be referred to:

TABLE 1

Example Types Hierarchy

| | |
|---|---|
| "Element" (Static Type) | "Brain Structure" (Dynamic Type) |
| | "Brain Structure coordinates" (Dynamic Type) |
| | "Patient" (Dynamic Type) |
| | "Brain Atlas" (Dynamic Type) |
| "Experiment" (Static Type) | "fMRI" (Dynamic Type) |
| | "DTI" (Dynamic Type) |
| | "Gene Expression" |
| "Relation" (Static Type) | "Connection" (Dynamic Type) |
| | "Gene Expression in Brain Structure" (Dynamic Type) |
| | "Patient Assessment" |

Editable Static Type

The Editable Static Type is a Static Type representing a user-customizable family of Dynamic Types. These allow the user to dynamically create, modify, delete, activate, and deactivate dynamic types belonging to this static type. The configuration of dynamic types for the editable dynamic types is stored in the database, and can be dynamically modified in run-time. All dynamic types of a specific editable static type have the same data model and behaviour. For example, the Static Type "Element" is an Editable Static Type.

Non-Editable Static Type

This is a static type representing a fixed family of dynamic types. As opposed to Editable Dynamic Types, the set of Non-Editable Dynamic Types of a specific Non-Editable Static Type is hard-coded and cannot be dynamically customized by the users in run-time. The purpose of the Non-Editable Static Type is to reuse the concept of Dynamic types in cases where the user customization of object types is not needed. The Static Type "folder" is a Non-Editable Static Type. All Dynamic Types of this static type are hard-coded.

Non-Editable Dynamic Type

This is a dynamic type belonging to the non-editable static type. As an example, the Dynamic Type "Element Folder" is a non-editable Dynamic Type of the non-editable static type "folder".

Singleton Static Type

The Singleton Static Type is a Static Type composed of exactly one pre-defined Dynamic Type. It is used for representation of arbitrary application objects as "Dynamically Typed Objects"—useful when a generic service provides functionality based on the notion of a dynamic type, and it is needed to reuse this functionality for application objects which are not dynamically typed objects. For example, the Static Type "user" is a Singleton Static Type and has only one predefined static type "user". Or, the Static Type "Query" is a Singleton Static Type and has only one pre-defined Dynamic Type "Query".

Elements

An element is an object of primary interest for the user. In the BioXM system, the primary goal of the user is to populate, collect, process, and analyze the information about Elements. Thus, an Element is a central notion in the BioXM system, acting as a "glue" for the rest of the application functionality. Most system functionality has the purpose of associating information with Elements, and providing the means for working with elements by working with their associated information. Elements can be thought of as "dummy entities": the information about elements is not stored within the elements, but instead is associated with elements by means of additional mechanisms as discussed herein (Annotations, Relations, Contexts, Experiments, for example). Each element belongs to a specific element type. Each element has a name unique in the scope of its element type.

For example, "Brain Structure", "Brain Structure Coordinates", "Patient" are elements of different element type. Brain structure "hippocampal formation" is an Element of Element type "Brain Structure". Brain structure coordinate "x0.1224_y12.4543_z4.0112" is an Element of element type "Brain structure coordinate".

Figure 4:
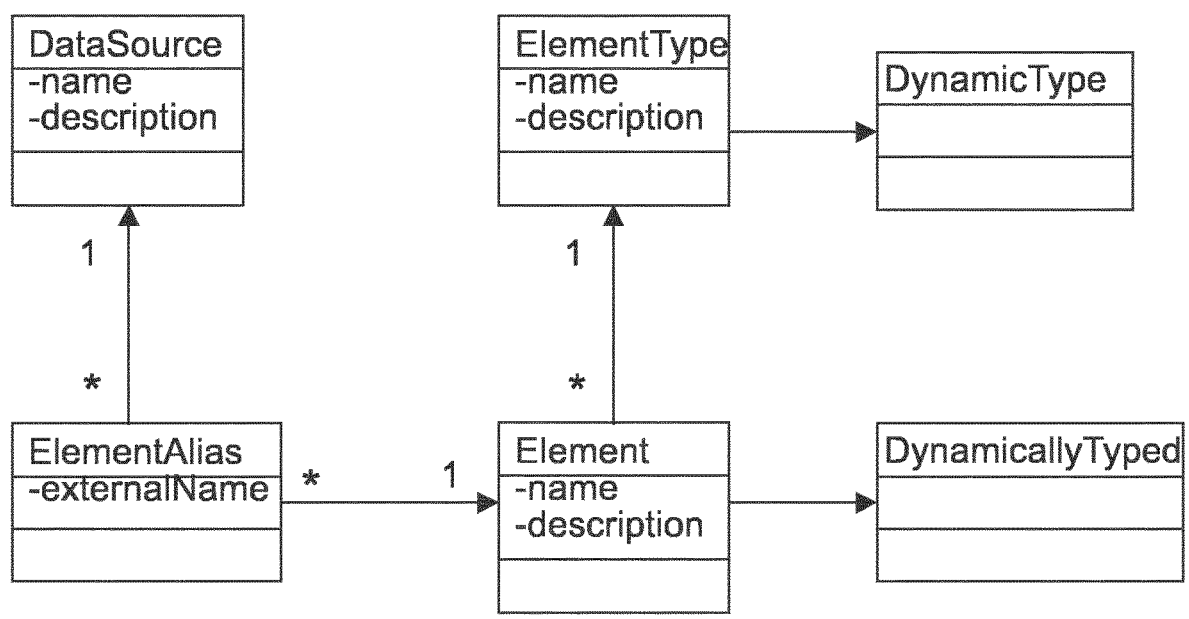
FIG. 4 illustrates an example of an Entity Relationship Model for the "Element" Module.

FIG. 4 illustrates an Entity relationship model for the "element" module. The "element type" is intended to classify different elements. The set of available element types can be dynamically customized. Element type plays a role of dynamic type for elements. For example, "Brain structure", "Brain structure coordinates", and "Patient" form element types.

Relations

Figure 5:
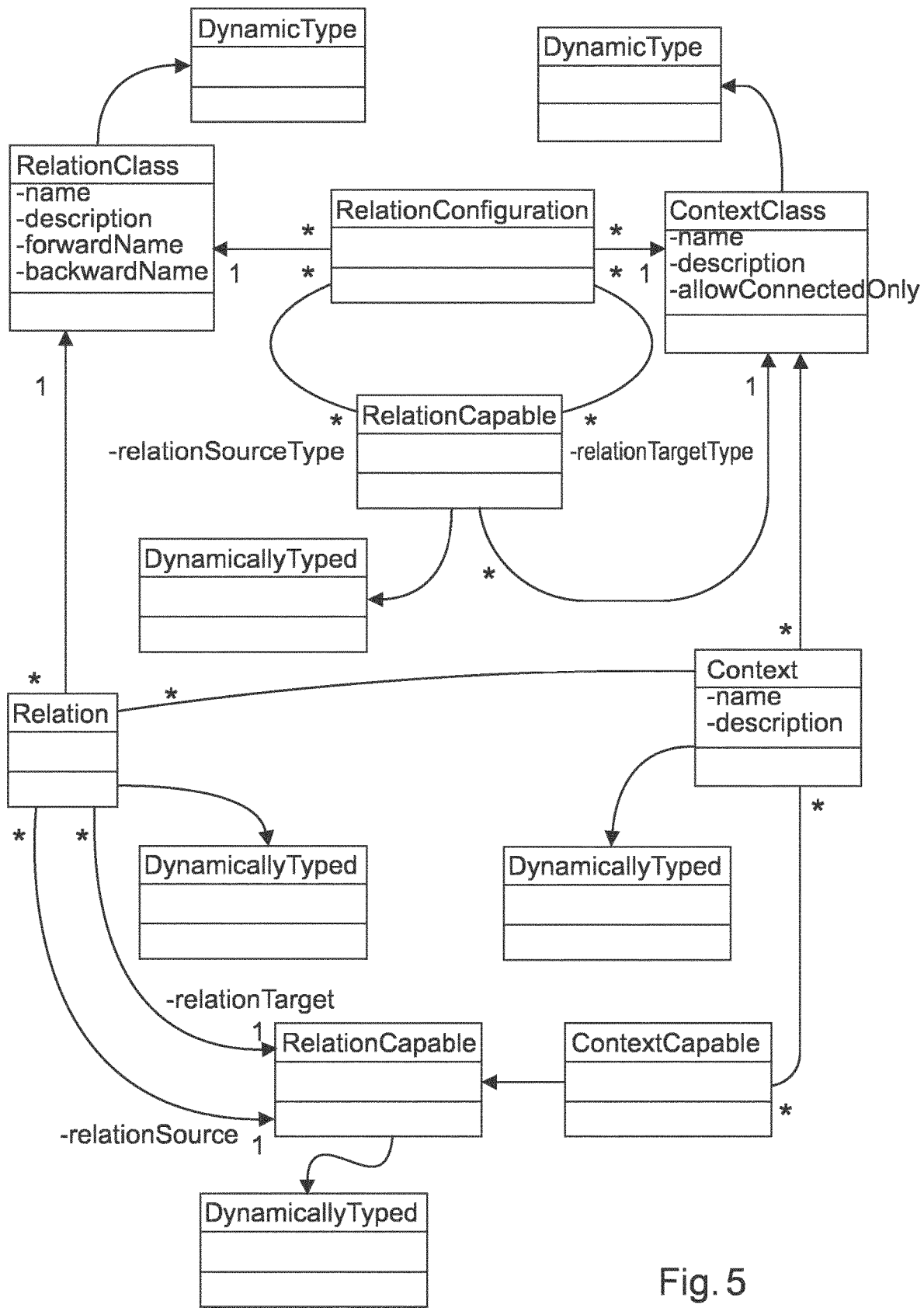
FIG. 5 illustrates illustrates examples of the Entity Relationship Model for the "Relation" module and the "Context" Module.

FIG. 5 illustrates the Entity Relationship Model for the "Relation" module and the "Context" Module.

A relation is a directed relation between relation subjects. Each relation represents the knowledge that two Objects (Relation Subjects) are logically connected in some way. The first Relation Subject plays the role of the Relation Source, and the second Relation Subject plays the role of the relation Target. Each relation belongs to a particular relation class. For example, the "Gene Expression in Brain Structure" has a relation source "Gene Expression" and a relation target "Brain Structure". The "Connection" is a recurrent relation with both the source and the target being the Element "Brain Structure".

A relation subject is the subject for the Relation Service—an entity, for which relations can be maintained by the relation service.

A relation source is the relation subject at the first position in the pair of relation subjects in a particular relation.

A relation target is a relation subject at the second position in the pair of Relation Subjects in a particular relation.

A relation class is intended to classify different relations. The relation class defines the set of relation configurations allowed by the relation class, only relations matching specified relation configurations may belong to this relation class. The set of available relation classes may be dynamically customizable. Thus, the relation class plays the role of a dynamic type for relations. Each relation class has two properties—one called forward name, and one called backward name—representing the semantics of the relation in forward and backward directions. For example, the relation class "brain mapping" contains all relations between any element types "brain atlas".

A relation configuration is the definition of a possible relation, defining pairs of object types for both the relation source and the relation target. For example, the relation "gene expression in brain structure" is defined by a forward definition "is expressed in" and a backward definition "expresses". Forward and backward definition are given by the direction of the relation, and can be easily flipped if necessary.

Graphs and Contexts

A graph is composed of Objects and Relations. Given a set of Objects (Relation Subjects) and Relations between these Objects, it is possible to say that a graph comprised of these Objects and Relations exists. Objects act as nodes, and Relations act as edges in the Graph. A Graph may be connected or disconnected.

A "world graph" is the graph comprised of all existing Objects and Relations. The World Graph is not necessarily a connected graph. It may be comprised of a set of disconnected sub-graphs.

A context is, for example, a saved and named graph. The existence of certain subgraphs in the World Graph represent valuable knowledge for users. This knowledge is saved in the form of Contexts. Contexts consist of the enumeration of Objects (Context Subjects) and Relations between these Objects. Saving subgraphs of the World Graphs as Contexts allows the user to work with these sub graphs in a convenient way.

Context Subjects exist in the Context. Single Context Subjects may be included into an arbitrary number of Contexts. Once a Context is created, it can be further modified reflecting the change of knowledge about Context Subjects (by adding or excluding Context Subjects and Relations to or from the Context). Each Context belongs to a specific Context Class. Each Context has a name unique in the scope of its Context Class.

The Context Subject is the Subject for the Context Service. It is an entity, for which contexts can be maintained by the context service. Optionally, it is referred to as a Context Capable Object.

A Context Class is intended to classify different Contexts. Context Class defines the set of Object Types and Relation Configurations, allowed by Context Class. Only Objects and Relations matching specified Object Types and Relation Configurations can belong to this Context Class. The set of available Context Classes can optionally be dynamically customized. Context Class plays the role of Dynamic Type for Contexts.

Annotations

Figure 6:
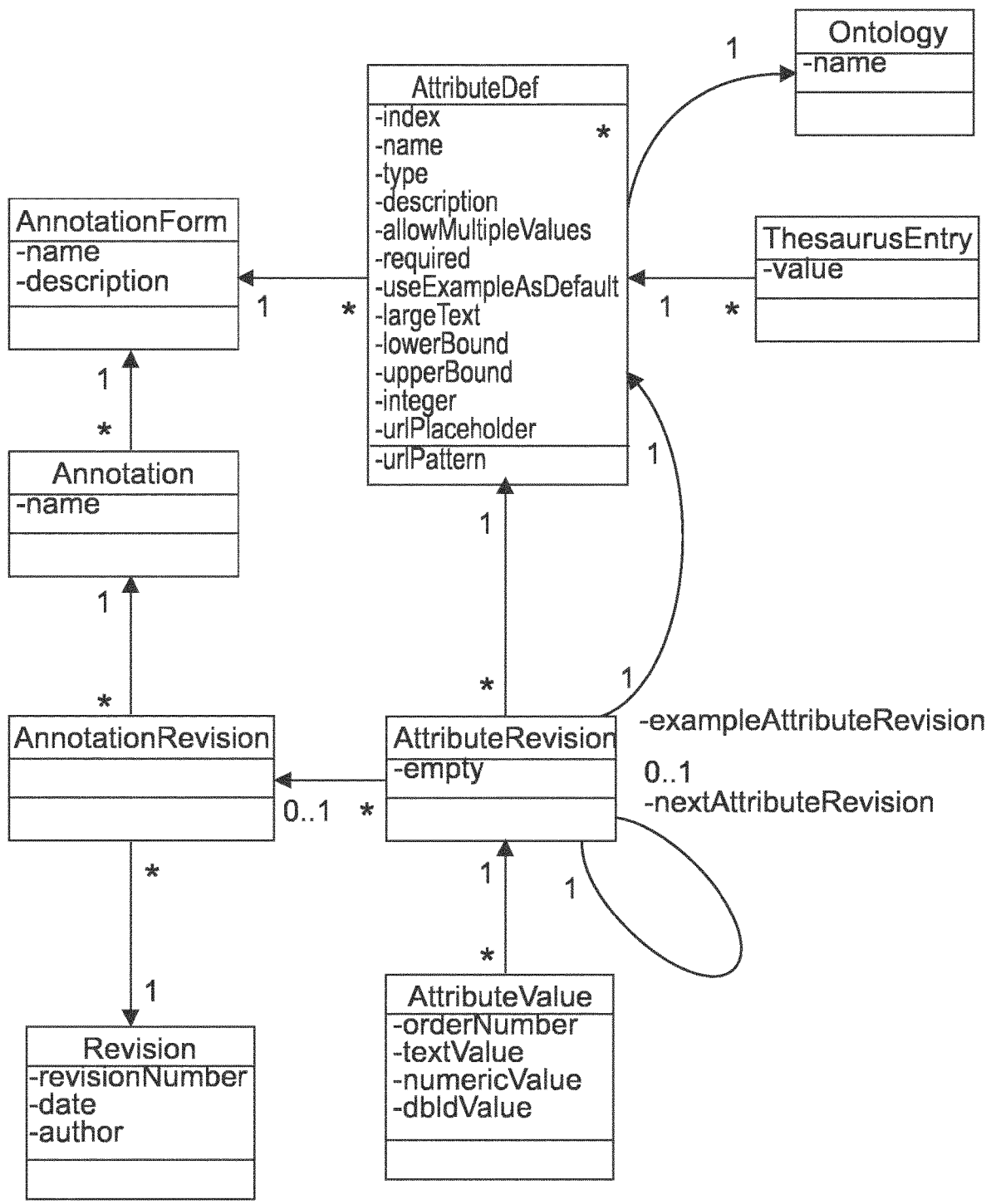
FIG. 6 illustrates illustrates an example of the Entity Relationship Model for the "Annotation Module".

FIG. 6 illustrates the Entity Relationship Model for the Annotation Model. For example, "Synonyms" can be added to Brain Structure as an annotation.

Figure 7:
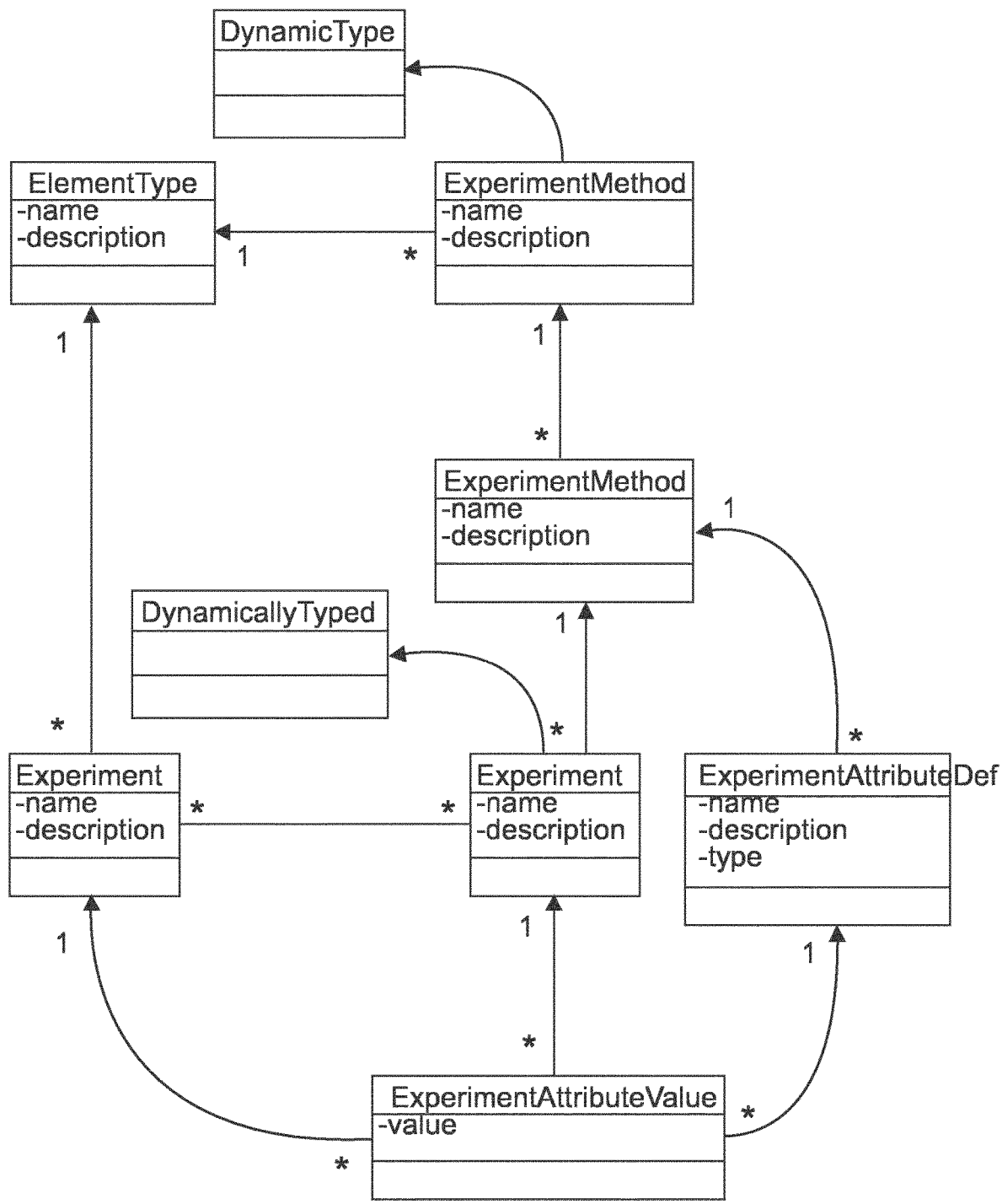
FIG. 7 illustrates an example of entity relationship model for the "Experiment Module".

FIG. 7 illustrates an entity relationship model for the Experiment Module. An Experiment is a set of data taken from Experimental Subjects (for example, "patient #1"). It contains the matrix of Experiment Attribute Values for a given set of Experiment Attributes, and a given set of Experiment Subjects. The set of Experiment Subjects is specific for each experiment. The set of Experiment Attributes is defined by the Experiment Format. Each Experiment belongs to a specific Experiment Format (for example, "fMRI scan") and a specific Experimental Method. Each experiment has a unique name in the scope of its Experiment Method.

The key feature of the Experiment is that it keeps experimental data for a set of Experiment Subjects at once, "gluing" this information together. An Experiment may have additional associated properties, such as experiment conditions, and so it is important that all relevant experiment data is glued together in a single Experiment Object. Experimental data is typically obtained by so-called "high-throughput" Experiment Methods, like fMRI or DTI scans.

The main purpose of experimental data is to use it for data mining (extracting new knowledge about experimental subjects), typically using a range of statistical analysis methods. For example, in the neurology application discussed in this application, an Experiment "Measurement_DTI" (DTI="Diffusion Tensor Imaging") that contains the data of the measured anatomical connection strengths of a Connection present in the measurement.

Experiment Subject

The subject for the Experiment Service is an entity, for which experimental data is maintained by the Experiment Service. This is also known as a "Experiment Capable Object". For example, The Experiment Subject of the Experiment "DTI" is the Relation "connection", because the strength of connections in the brain of an Experimental Subject was measured. The Relation is the Experiment Capable Experiment.

Experiment Method

The Experiment Method defines how the experimental data is produced. The Experiment Method is intended to classify Experiments. Each Experiment Method is intended to obtain experimental data for a specific Experimental Subject Type. All experiments of an Experiment Method may contain experimental data only for Experiment Subjects of the Experiment Subject Type specified by the Experiment Method. For different Experiment Subject types, there are different Experiment Methods. For a specific Experiment Subject Type, there may be a number of different Experiment Methods. The set of available Experiment Methods may be dynamically customized. The Experiment Method plays the role of Dynamic Type for the Experiments. Thus, for example the Method of the Experiment "Measurement_DTI" is "DTI".

Experiment Attribute

An Experiment Attribute is an attribute of the Experiment Subject, whose values are contained in the experimental data. Experiment Attributes are defined by Experiment Formats. Each Experiment Attribute has a name (unique in the scope of the Experiment Format) and a type. Possible types of Experiment Attributes are integer numbers, floating point numbers, and text. For example—Experiments of the Experimental Method "DTI" (Diffusion Tensor Imaging) have an Experiment Format "Measured Fibre Density" which can be further specified by the Experiment Attributes "Absolute Value" and "Normalized Value".

Experiment Attribute Value

The value of Experiment Attribute for a certain Experiment Subject in an Experiment. The type of Experiment Attribute Value should match the type specified in the definition of Experiment Attribute in Experiment Format.

For example, the "absolute value" holds Experiment Attribute Value as the measured value that comes from an imaging experiment.

Object Type Capabilities

Figure 8:
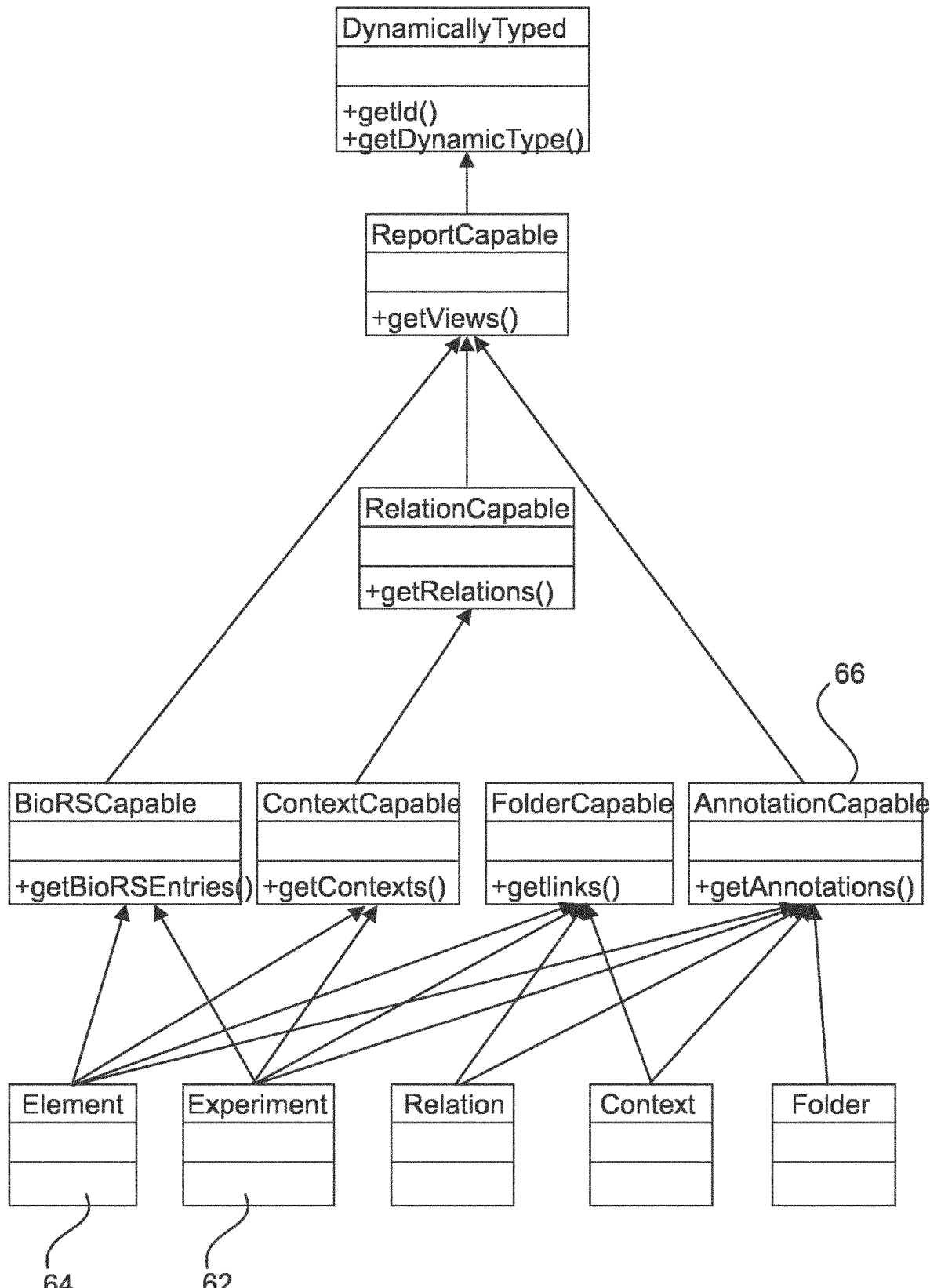
FIG. 8 illustrates examples of the BioXM platform type capabilities.

FIG. 8 illustrates BioXM Type capabilities. It is seen that modules can implement certain interfaces, adding specific capabilities. For example, Elements, Experiments, Relations, Contexts, and Folders implement the "AnnotationCapable" interface, enabling objects of these types to be subject to the Annotation service.

In a simple implementation example, this means that experiment 62 holds data from the outcome of an fMRI scan of a patient. In addition, element 64 is a link to a gene database such as the "Human Allen Brain Atlas", containing gene expression data, optionally at specific points in 3D space in a "control" human brain. The fMRI data (once post-processed) comprises a series of connection strengths between points inside a 3D space containing human brain tissue. The element 64 and experiment Objects 62 have links to the "AnnotationCapable" interface 66, meaning that in one sense, specific connections in the fMRI data may be annotated with gene expression data linked to the presence of a connection in the fMRI data. Of course, because of the directed nature of relations in the knowledge model, the model may be inverted, and it is possible to query fMRI experiments (one, or a plurality, for the same patient, or for different patients) based on the expression of a certain Gene in the Human Allen Brain Atlas. Thus, with the same knowledge model, it is possible to perform a "clinical" task or a curiosity-driven "research" task. Critically, the gene database, or new fMRI measurements, may be easily added to the knowledge model at any time, easily enabling an increase in the utility of the model.

Thus, in an example, a relation "gene expression in brain structure" is used to link a gene expression experiment to an individual brain area. Each relation for every individual gene expression measurement is annotated by the 3D-coordinates at which position relative to a normalized standard brain (NMI-152 brain) the tissue sample was taken from. A further annotation of each brain structure is made using its preferred name, synonyms used in literature, and centre of mass coordinates of the entire area.

Data Import

The framework of the knowledge model discussed above is also provided with a "data importer" enabling the efficient population of the various Elements and Objects with data. The data importer is configured to import standard file formats such as OWL (Web Ontology Language), OBO (Open Biological Ontologies), OPMP (Outline Processor Mark-up Language), for example.

Alternatively, via the GUI, a wizard-guided import of tabular data is possible, which enables the upload of data in many formats, including Excel®, Open Document, or plain text. A graphical import script builder allows an instruction set to be created and applied to every table row during import. Furthermore, import scripts can be customized by a user to execute complex tasks during import, such as deleting objects, transforming relations, and annotation of data to other objects.

The BioXM framework, upon which the NeuroXM system is implemented, integrates the BioRS retrieval component, which provides a transparent mechanism to integrate external relational, or flat-file databases and text sources. The BioRS middleware supports commonly used public database formats, such as "Entrezgene", "PubMed", and "PubChem".

Alternatively, the BioXM/NeuroXM system provides all necessary Application Programming Interfaces (APIs) to integrate applications or databases as "virtual objects".

Optionally, an embodiment of a more complex data import capability is provided as the tab importer. In brief, this enables the user to generate a script which defines the semantic role of import data columns. Thus, as the import occurs, the transformation of the data into semantic data, and the attributes and connections of the data to the existing semantic model, may be assigned.

To use the tab importer, object types are first defined for objects that will be populated with imported table data. Relation classes and assignments are defined for connections to be created between objects in the data. Annotation forms can be defined for table data that will be used as an annotation. Then, the relevant external data source is chosen with a GUI wizard or a command line. A script to define the link between entries in the data table to be imported, and the existing knowledge model, may be defined. Optionally, data import operations that can be defined by the import script comprise one or more of (i) the creation or lookup of objects in the semantic network, (ii) the modification of existing object properties, (iii) annotations of objects, (iv) knowledge processing—the creation of semantic connections between objects in the knowledge model, (v) data deletion, (vi) project and resource maintenance, and (vii) execution control (manipulating the workflow of the import script based on the content of data previously imported).

Optionally, the tab importer enables the definition of an import processing policy, so that the import into the knowledge model of large (>GB) files can be monitored.

Implementation Options

It will be appreciated that a semantic network of the type discussed above can be implemented using a database running on computer hardware, with associated computer hardware for inputting information and visualizing results. In a first variant, the client tier 10, server tier 20, and database tier 30 are stored and executed on the same computer equipment. Optionally, a smartphone, tablet computing device, or other appropriate equipment could be used.

In a second variant, the client tier 10 is stored and executed on a first computer, and the server tier 20 and the database tier 30 are stored and executed on a second computer, which may optionally be located geographically remotely to the first computer storing and executing the client tier 10. The first and second computers may be linked by a functional data connection maintained over a Local Area Network or a Wide Area Network which is capable of supporting communication between the client tier 10 and the server tier 20 using at least the IIOP communication protocol, for example.

Figure 9A:
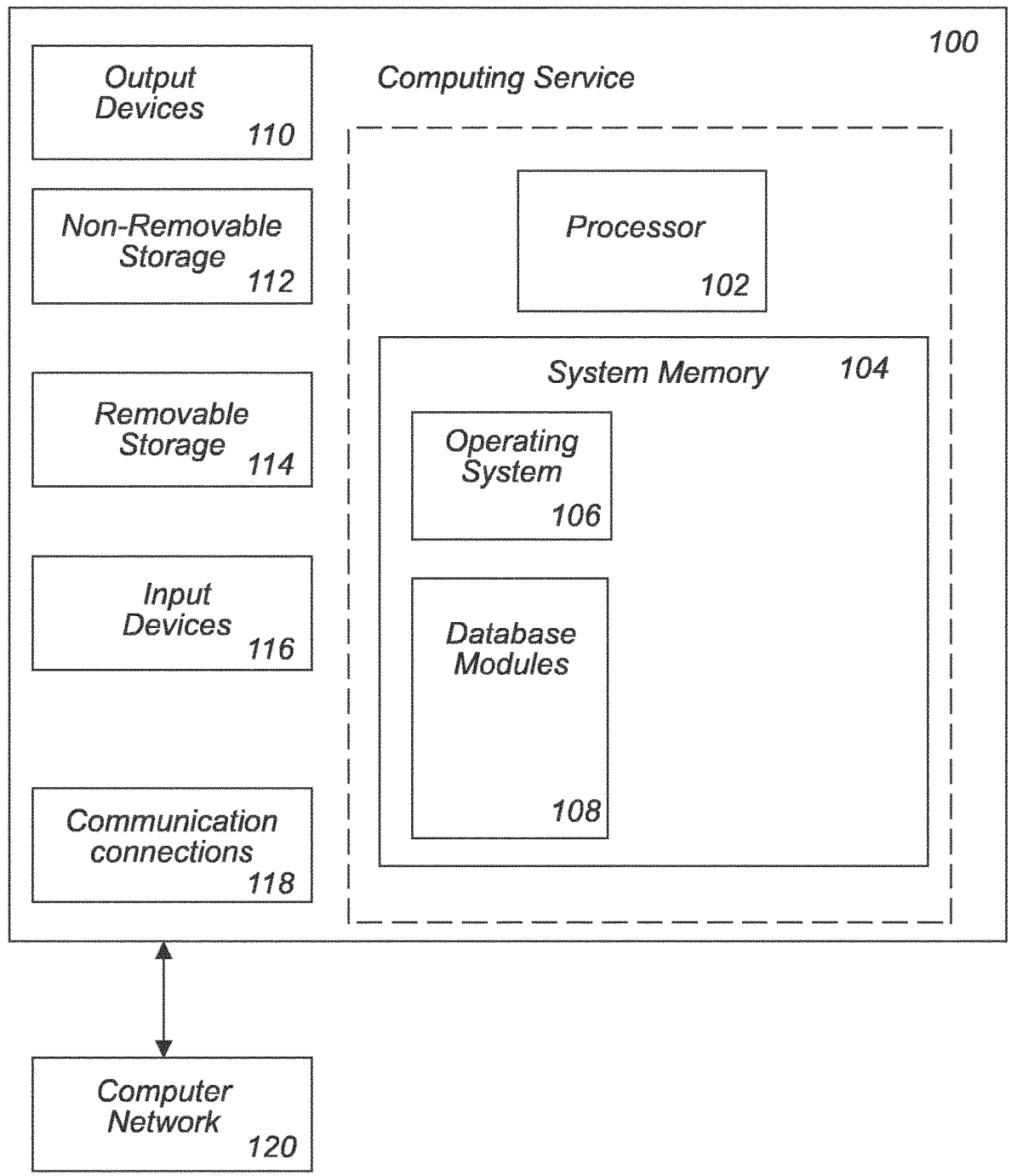
FIGS. 9a) and 9b) illustrate examples of a computer and computer network implementation of the BioXM system, respectively.

FIG. 9a shows a block diagram illustrating the physical components (hardware) of a computing device 100 upon which embodiments of the present invention may be implemented. Optionally, and as noted in the previous paragraph, computing device 100 may implement the client tier 10, server tier 20, and database tier 30 of the knowledge model. Alternatively, computing device 100 may implement the client tier 10, and communicate with an external computing device (not shown in FIG. 9a), which may be of the same general disposition as the computing device 100 but configured to implement that server tier 20 and the database tier 30.

Computing device 100 comprises, in a basic configuration, a processor 102 and system memory 104. The system memory 104 may be volatile storage, non-volatile storage, flash memory, or a combination of these. Operation of the computing device 104 may result in an operating system 106 being loaded into the system memory 104. The operating system may contain database modules 108 (a software module) enabling operation of the semantic knowledge model discussed herein. Typically the database modules 108 are implemented using a SQL-derived database, but others will be known to the skilled person. The operating system 106 may, for example, be capable of controlling the operation of the computing device 100.

A number of database modules and program files may be held in the system memory 104. While executing on the processor 102, the database modules 108 may perform processes including, but not limited to, any one of the stages of the methods and processes discussed herein or illustrated in the figures.

Furthermore, embodiments of the computing device 100 may be provided as a general purpose computer comprising packaged electrical circuits comprising logic gates, a microprocessor, a general purpose microprocessor as, for example, supplied by Intel®, or on a System on Chip (SOC).

The computing device may also have output devices 110, such as a display, a printer, loudspeakers, and the like. The computing device may also have input devices 116 such as a keyboard, a mouse, a touch-screen, or a microphone.

The computing device may also have a removable storage interface 114 suitable for interfacing with computer readable media. Computer readable media includes volatile and non-volatile memory, suitable for storing computer-readable instructions, data structures, and program modules. It may include Flash Memory, CD-ROM, DVD, DVD-R, other optical storage media, USB memory sticks, magnetic cassettes, magnetic tape, magnetic disk storage such as a removable hard-drive, computer network disks, any of which can be used to store information and be accessible by the computing device 100. The computing device may also have non-removable storage 112 suitable for the operation of the computing device 100 such as RAM, EEPROM, magnetic disk memory, and the like.

The computing device 100 may also have communication connections 118 such as an Ethernet interface, WiFi connections, USB, and other interfaces enabling the connection of the computing device 100 to an external computer network. The computing device may also be connectable to a computer network 120.

Figure 9B:
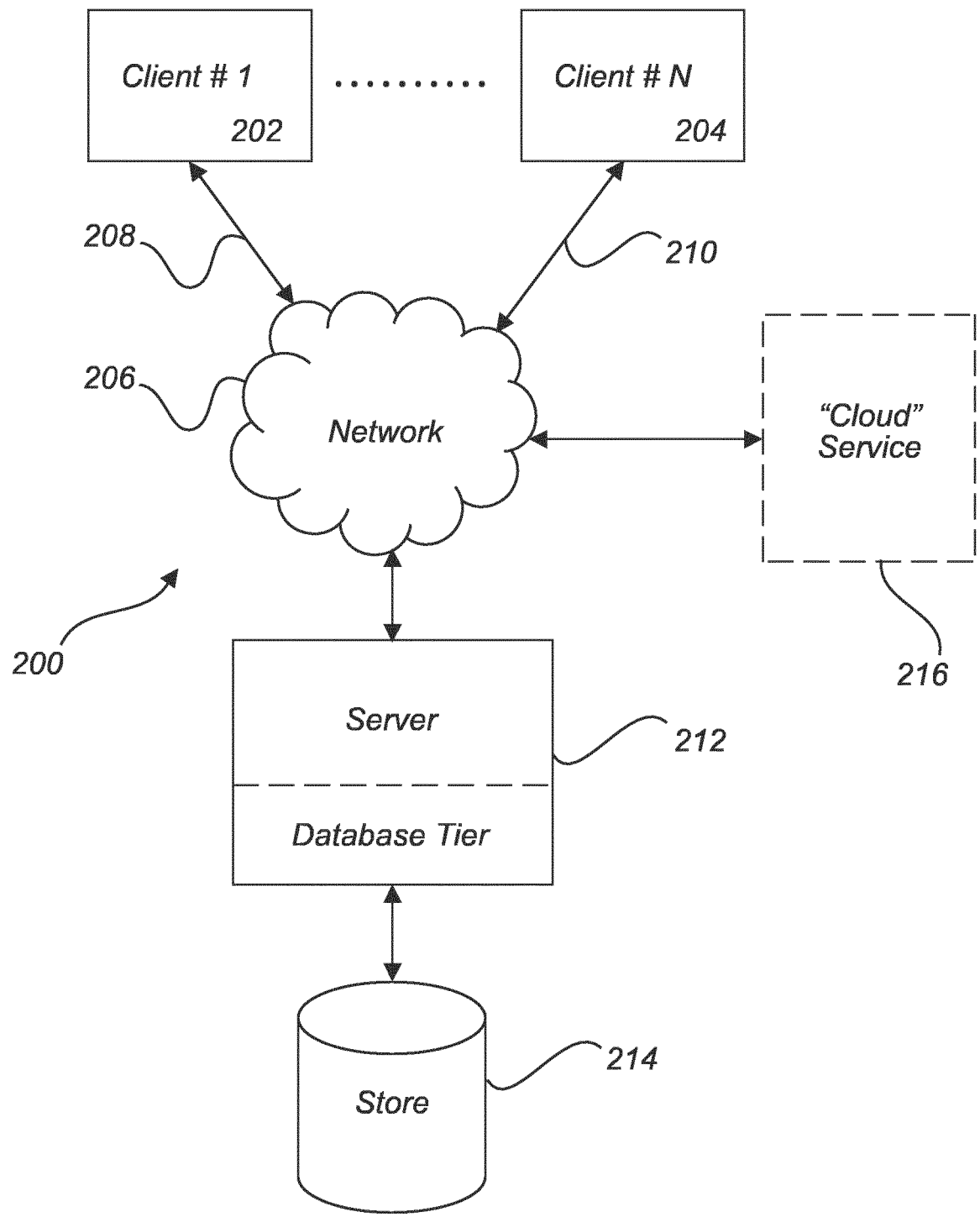

FIG. 9b illustrates a client-server network 200. The client-server network 200 comprises a first client 202 and a second client 204 according to the description in FIG. 9a, although a large number of clients may be supported. The first client 202 and second client 204 are configured to communicate with a network switching fabric 206 via communication links 208 and 210, respectively. Communication links 208 and 210 to the network switching fabric 206 may be Ethernet connections, WiFi connections, and the like, enabling communication with a distant server through the network switching fabric 206 using a networking protocol. Exemplary networking protocols are TCP/IP or UDP, although other protocols will be known to the person skilled in the art. Thus, the network switching fabric 206 may contain, for example, a hierarchy of switches, routers, network servers and the like to ensure that data can be transferred between the clients 202 and 204 and the server 212 in a timely manner. The server 212 may be connected to a data store 214 enabling long-term storage of large data files. In addition, the server 212 and/or the clients 202 and 204 may be connected to a "cloud" computing service 216 enabling the remote storage of data, or even the remote computation of information.

In practice, the client tier 10 of the BioXM installation previously discussed would be implemented on the first client 202 and optionally the second client 204. The server tier 20 and the database tier 30 of the BioXM installation would be implemented on the server 212, although optionally the server tier 30 could be "split off" into yet another server for reasons of load-balancing, for example. It is to be noted that this description is simply one practical embodiment of the discussed technique. In other examples, the entire framework of client tier 10, server tier 20, and database tier 30 may be performed on the same computing device, for example. In addition, the computing devices of the client tier 10 may be "smart phones", or "tablet computing devices", for example.

First Aspect

It will be understood that features, embodiments and options of the foregoing discussion of the knowledge model are combinable with the following discussion of the present invention and/or support the subject-matter of the claims.

Therefore, according to a first aspect, there is provided a computer-implemented neurological data processing method comprising:

a) acquiring 300 first element data and second element data representing, respectively, attributes of a first location and a second location in a subject vertebrate brain;

b) acquiring 302 neural connectivity data linking the first element data and the second element data, wherein the neural connectivity data comprises a representation of a functional and/or structural connection between the first location and the second location in the subject vertebrate brain, and wherein the first element data, second element data, and the neural connectivity data form a semantic network;

c) acquiring 304 annotation data comprising object data;

d) mapping 306 the annotation data to the neural connectivity data to thus generate neurological knowledge model data related to the subject vertebrate brain, wherein the neurological knowledge model data is a semantic network capable of being queried using a formal linguistic specification, wherein the formal linguistic specification is derived from the semantic network; and e) outputting 308 the neurological knowledge model data.

Figure 12:
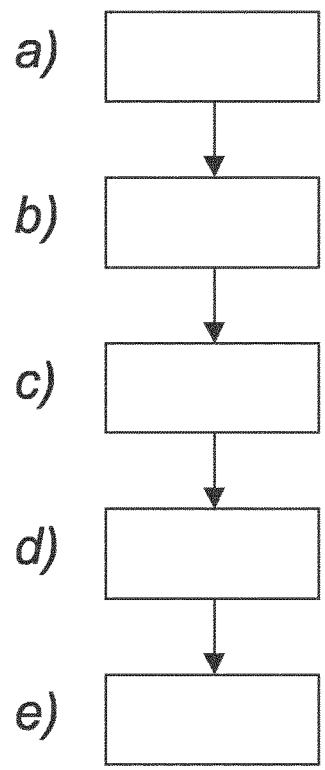
FIG. 12 illustrates the method according to the first aspect.

FIG. 12 illustrates the method according to the first aspect.

In step a), the step of acquiring data representing first element data and second element data may, for example, be performed using the import of a DTI file obtained from a corresponding scan of a patient. Optionally, this data may be imported into a knowledge model using the data importer. The DTI data may be stored as "Experimental Data". The attributes of the first location and the second location in the subject vertebrate brain may comprise the "x,y,z" coordinates in the brain, for example.

In step b), the step of acquiring neural connectivity data linking the first element data and the second element data may, in an option, be derived from the same DTI file as used in step a). The DTI "Experimental Data" is, prior to loading into the knowledge model, post-processed using an appropriate algorithm, as known in the art, to extract fibre connectivity derivable from the DTI images. Thus, Experimental Data "DTI" contains a measured structural connection strength in terms of a correlation value of neural connectivity of the two brain areas as derived from the DTI image. The neural connectivity data may thus contain, for example, a relative fibre connectivity of a neural fibre bundle between the location of the first element or the second element.

Optionally, the neural connectivity data may also, or in addition, be fMRI data, to provide functional information. FIG. 1a) shows a visual example of a table of neural connectivity data nodes of a human brain obtained via DTI imaging and appropriate post-processing. In FIG. 1a), the positions on the x-axis delineate a row vector of a first set of voxels in the neurological data (which can be approximated to nodes) present in an DTI scan. The positions on the y-axis delineate a column vector of nodes of a first set of voxels in the neurological data. The intensity of the "boxes" in the body of the graph relates to the strength of a neural connection made between the nodes. In other words, an entry on the x-axis represents a "first element", an entry on the y-axis represents a "second element", and the intensity of the intersecting box in the graph represents neural connectivity data linking the first element data and the second element data. In other words, the "first element" and "second element" are first and second instances of the BioXM object "Element". They are connected with a BioXM Relation "Connection". The Relation "Connection" denotes in this case a structural connection between the two brain areas.

It may already be seen that the first element data, second element data, and the neural connectivity data form a semantic network, because it is possible, knowing the first element and the second element, to obtain knowledge of the strength of the axonal connection between those elements. Looked at another way, is possible to interrogate the semantic network with a threshold, to identify node pairs in the connectome that are above a certain neural (axonal) connection strength.

The advantage of the approach used in this application lies in the mapping of annotation data to the neural connectivity data. Using the flexible and configurable approach of the knowledge model discussed above, the annotation data mapped to the neural connectivity data may be very varied.

In this specific example, the Relation "Connection" is annotated by anatomical information which may, optionally, be taken from brain atlases, or anatomical ontologies. For example, the "Connection" can be annotated with the name of a fibre tract.

The mapping process of step d) results in a neurological knowledge model data which is a semantic network capable of being queried using a formal linguistic specification. In other words, the simple knowledge model of this example may be formally queried using a query term present in the brain atlas or anatomical ontology to which the annotated neural connectivity data has been mapped. Thus, a specific neural connectivity present in the experimental data can be identified on the basis of the query. The formal linguistic specification is derived from the semantic network itself, which means that brain structures not formally denoted in the brain atlases which are mapped to the annotated neural connectivity data may not be queried, for example.

In step e), following the mapping of the neurological knowledge model data to the annotated neural connectivity data, it may be considered that new, or updated neurological knowledge model data has been generated, and this may be output for further use. Typically, this data is in the form of a computer database. Many forms of output format are possible. One example is the Biomax semantic knowledge model database format.

It is observed that the process outlined above is highly flexible because it is based on a semantic network approach, as is clear from the discussion of the implementation of the ontological database discussed above. At any time, another updated patient DTI scan from the same patient, although from a subsequent time, may be loaded into the semantic network as a subsequent patient experiment. Then, it may be possible to identify changes in brain structure between the first and second experiments, and what anatomical implication the changes have had. The model is flexible, based around the central concept of mapping the annotation data to the neural connectivity data. Thus, large input data files may be automatically re-ordered and re-organized in such a way as to make information extraction from them quicker and more accurate. In addition, it may be possible for a user to discover connections between large bodies of information that they were not aware of initially.

Another example of the proposed technique lies in the making the Relation "Connection" in the above example the subject of Experimental Data "fMRI"—a functional image of the same patient. Experimental Data "fMRI" contains a measured functional connection strength in terms of functional correlations between anatomical brain areas, derived from the fMRI (derived again from MRI images).

Another example of the proposed technique concerns using a Relation "Brain Mapping" to connect every Element "Brain Structure" with an Element "Freesurfer" (Freesurfer is an anatomical brain atlas). In this way, anatomical significance of the annotated neural connectivity data can be discovered. Other atlases, such as the AAL atlas, the Craddock atlas, or the Glasser atlas defining the parcellation of the brain ("A multi-modal parcellation of human cerebral cortex"—Glasser, M, et. al, Nature2016/08/11/print, vol. 536, http://dx.doi.org/10.1038/nature18933).

Optionally, the first and/or the second element data may be annotated with the Relation "Brain Mapping" to connect every "Brain Structure" to the Ontology "Human Allen Brain Atlas", and/or to the Ontology "Neurodomain of the Functional Model of Anatomy", thus annotating the element "Brain Structure" with a hierarchically organized terminology. Via this relation, references are created between multiple brain structure Elements.

Another example application of the proposed technique uses the semantic network by annotating the neural connectivity data using the Relation "Gene Expression in Brain Area". This relates a Brain Structure to Experiment Data "Gene Expression" storing measured gene expression values from brain tissue derived from this brain structure, for example as available from the microarray data of the "Human Allen Brain Atlas". Further Relations could relate Experiment data "Gene Expression" to elements "Gene" and to "Neural Receptor Protein".

Optionally, step a) comprises acquiring a dataset representing a subject vertebrate brain.

Optionally, in step a), the first element data and second element data are comprised in a connectome dataset.

Optionally, in step a), the first element data and second element data represent voxels of a brain image.

Optionally, neural connectivity data is neuronal structure data.

Optionally, in step a), the first element data and second element data represent parcellated regions of a brain image.

Optionally the anatomical brain atlas data is based on an adult vertebrate brain.

Optionally the anatomical brain atlas data is based on a developing vertebrate brain.

Querying the Neurological Knowledge Model Data

Having formed the knowledge model, Elements and Relations can now be used to query the stored and processed data. The query input may be entered using a keyboard or GUI display element. Alternatively, the query may be held in a "Folder" Element which is continually searching for the answer to the query and updating the folder as the semantic network evolves, for example.

Thus, according to an embodiment, a computer-implemented neurological data processing method is provided as discussed above, further comprising:
f) acquiring query data encoding linguistic descriptors of primitives in the element data from a user.
g) mapping the query data onto one or more items of element data in the neurological knowledge model; and
h) generating query result data based on the mapping of the query data onto one or more items of element data in the neurological knowledge model data using the formal linguistic specification derived from the semantic network. Optionally, the method further comprises i) outputting the query result data.

Thus, the database containing the neurological knowledge model may be queried from many different perspectives, where the query language, in an example, constrained by the items of information present in the semantic network. As an example, a the presence of an fMRI data object in a semantic network implies that the semantic network may be queried at least with 3D locations in a subject brain as parameters. Or, adding a brain ontology to the semantic network means that the fMRI data could be queried using brain regions as parameters. As noted above, the queries may optionally be entered into the system using a linguistic descriptor in natural language format. For example:

"Find all elements "Brain Structure" that are connected by a connection strength (correlation value) larger than 0.7 to an Element "Brain Structure" that is related to Experimental Data "Gene Expression" that express a "Gene" which encodes for an Element "Neural Receptor Protein" which has a name "fkbp5"".

This query would be useful, because the gene "fkbp5" is proposed to have a role in schizophrenia. Finding not only all brain areas which express this gene, but also those areas which are strongly connected to the gene expressing brain areas, can reveal brain networks with a role in schizophrenia.

As a second example of querying the semantic network, a query may be: "Find all Elements "Neural Receptor Proteins" that are encoded by an element "Gene" which has a "Gene Expression" level greater than 5 and which is expressed in any Element "Brain Structure" which is labelled by an Ontology entry "frontal lobe" and which is connected with a normalized anatomical connection strength measured by DTI greater than "0.8" and a functional connection strength (correlation value) greater than 0.7 measured by (resting-state) fMRI to the Element "Brain Structure" with a name like "Amygdala"".

This query would be useful because the brain structure "Amygdala" is involved in the generation of emotions, while multiple brain areas in the frontal lobe enable the subject of experiencing the conscious feeling of arising emotion. Finding neural receptor proteins highly expressed in these areas relevant in processing feelings may offer a potential pharmacological target for treating mood disorders.

Figure 10A:
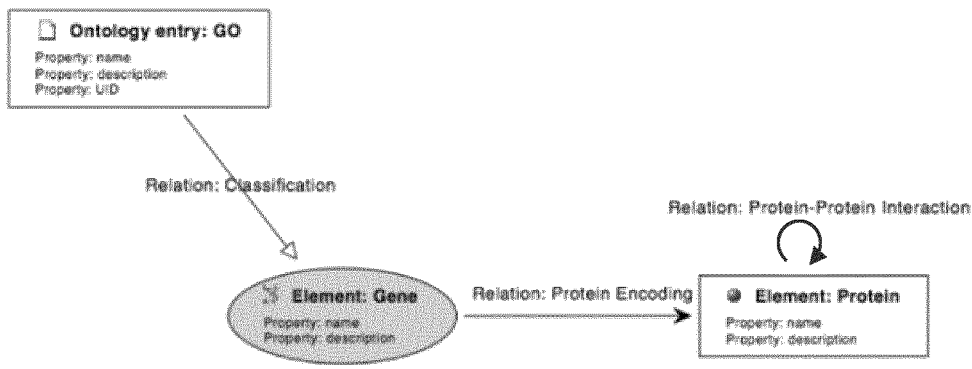
FIG. 10a) illustrates an example of a GUI interface to a semantic network between a gene element and a protein element in the BioXM ontology.
Figure 10A:
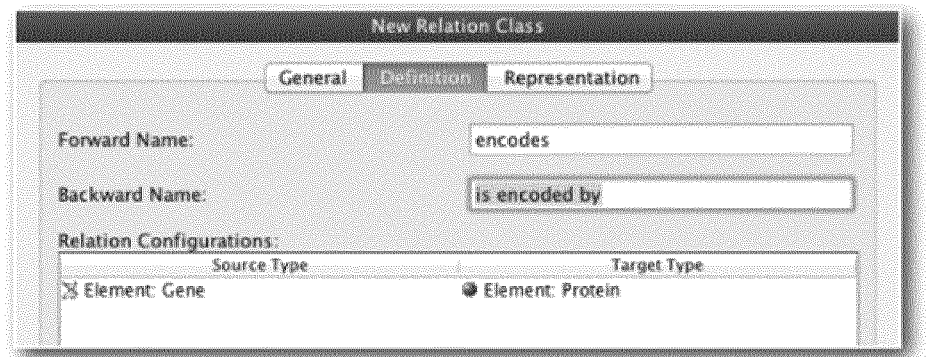

FIG. 10a) illustrates an example of a GUI display for a knowledge model. In this case, the knowledge model is a relatively simple one involving a gene element, a protein element, and a gene-protein element encoding derived from a database such as a "Human Allen Brain Atlas". An fMRI experiment for a specific patient could easily be added into this knowledge model, enabling the gene-protein expression to be compared with a specific functional connection in a human brain.

Figure 10B:
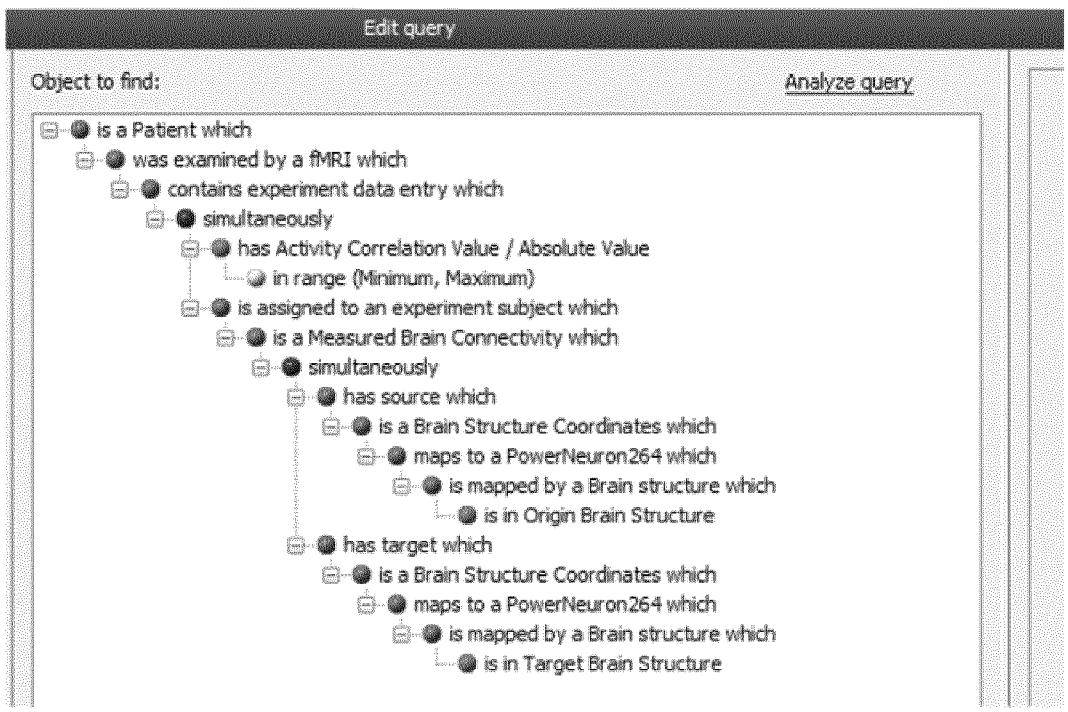
FIG. 10b) illustrates an example of a natural language query built in a GUI, using the formal language derived from a semantic network.

FIG. 10b) illustrates the GUI used to enter natural language queries for a specific instance of a populated knowledge model based on an fMRI patient experiment. As the database is extensible, the ontology available for querying the knowledge model will change as the knowledge model has items added or subtracted. In this case, the knowledge model involves at least an fMRI scan of a patient, and an imported brain structure atlas.

Figure 11A:
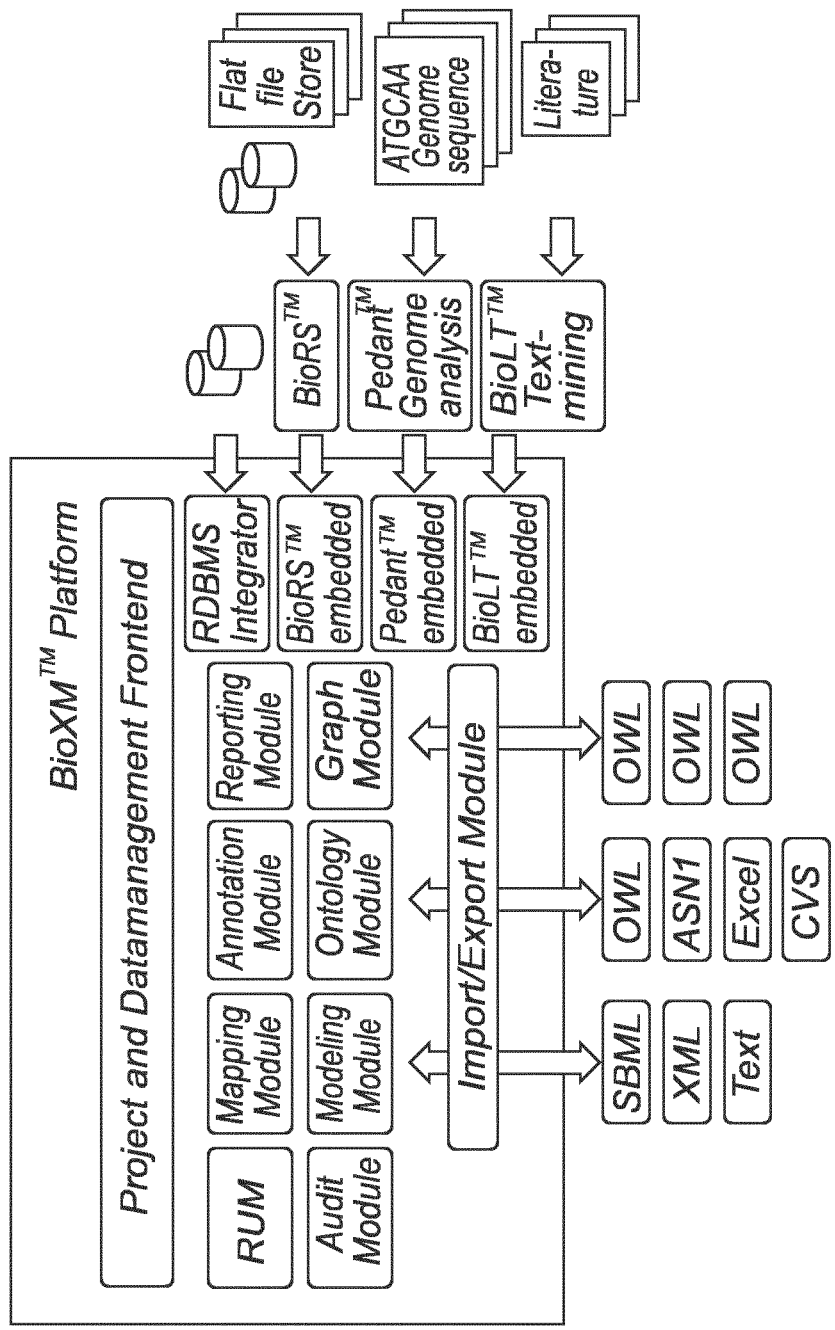
FIG. 11a) shows an example of the integration of BioXM platform modules with external information sources.

FIG. 11a) illustrates an example configuration of the BioXM platform, showing the relationship of the modules to input and output data options.

Figure 11B:
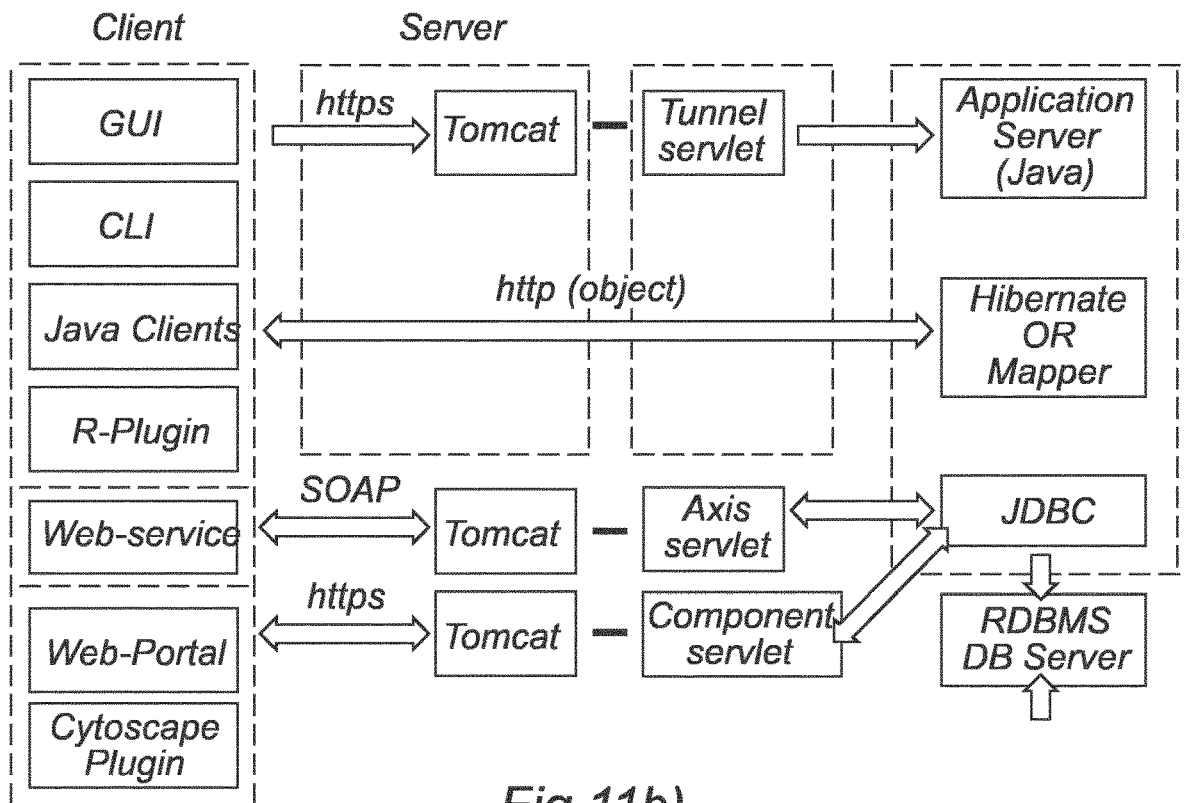
FIG. 11b) shows an example of the client-server messaging model of a typical BioXM implementation.

FIG. 11b) illustrates an example arrangement of the client-server data communication pathways and example communication protocols used for communication in the BioXM system.

Figure 13A:
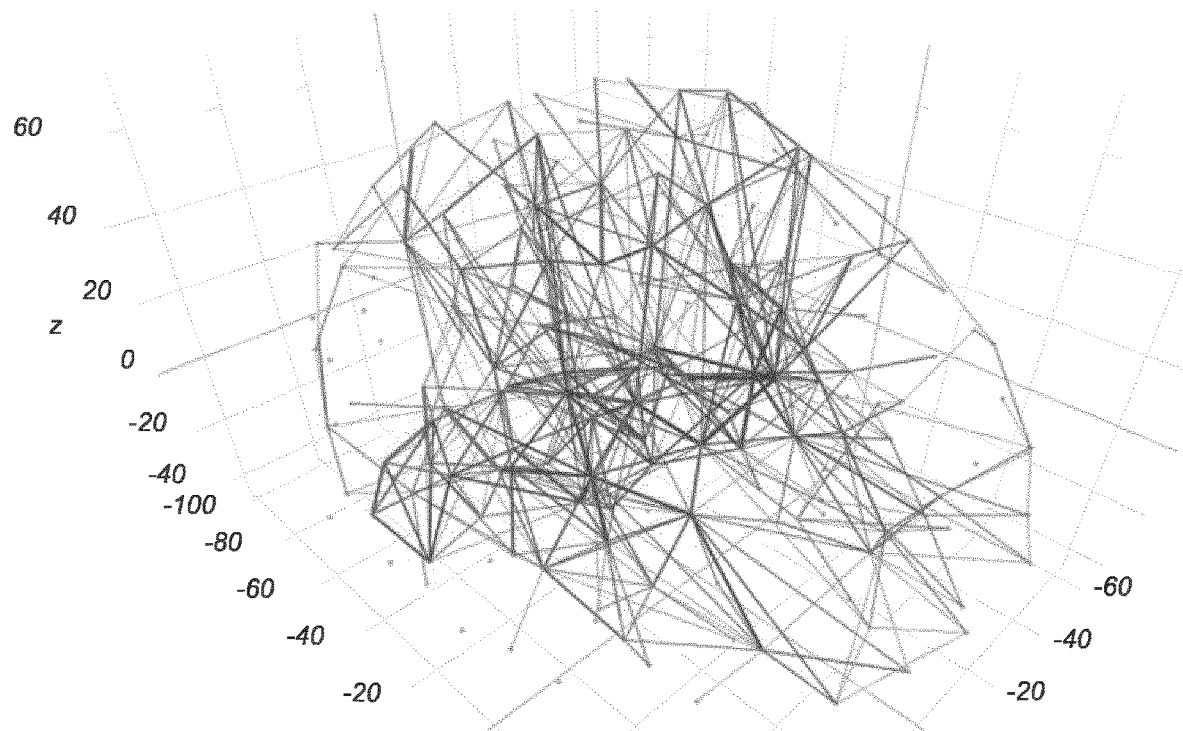
FIG. 13a) illustrates an example of output data of a query of the neurological knowledge model data.

FIG. 13 illustrates the use of a semantic network populated with patient functional imaging data and a semantic brain atlas. In this case, an anatomical circuit has been discovered in functional data of a selected patient by querying "limbic lobe" from an atlas. A 3D output map of the selected connections to the limbic lobe can then be displayed.

Figure 13B:
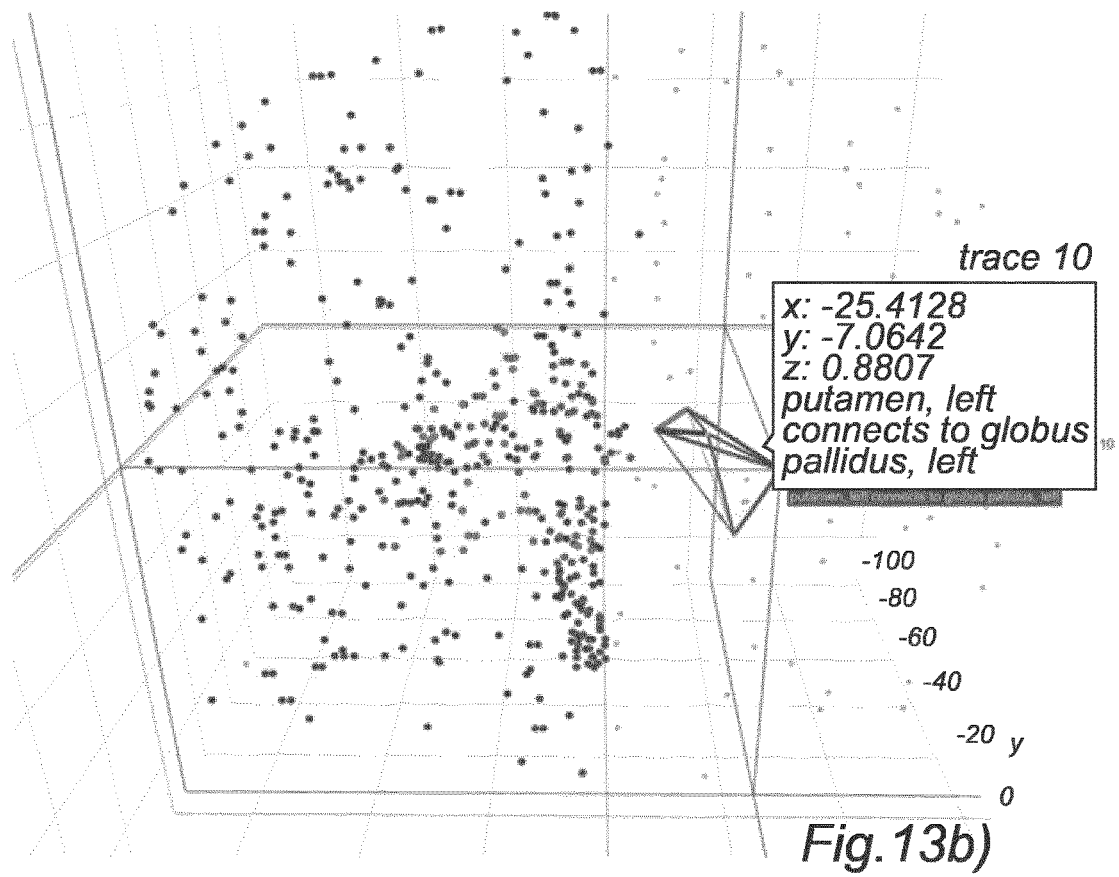
FIG. 13b) illustrates a further example of output data of a query of the neurological knowledge model data.

FIG. 13b) illustrates an example of the result of a query, as a 3D plot. In this case, dots of different intensity (or colour) represent the gene expression level of the neural receptor protein dopamine D2—the main target for the drug neuroleptikum haloperidol used in schizophrenia therapy. Grain dots are measured brain coordinates, and coloured lines are measured neural functional connections between measured brain coordinates. Line thickness codes for the anatomical or structural connection strength, and the colour code indicates the functional connectivity measured by different measuring techniques such as DTI and fMRI.

Input Data Sources

Many forms of input data can be added into the semantic network. In terms of brain imaging modalities, the following will be briefly discussed:

Functional Magnetic Resonance Imaging (fMRI) fMRI essentially detects changes in blood flow in the brain, because highly oxygenated haemoglobin responds differently to a strong magnetic field, as opposed to weakly oxygenated haemoglobin. Thus, levels of brain activity can be inferred from an fMRI image. Optionally, the experimental data comprises Functional Magnetic Resonance Imaging (fMRI) data.

Diffusion Tensor Imaging (DTI) examines the diffusion of water in tissue to identify the likelihood of a certain portion of tissue containing a neural tract (it is inferred that water is more likely to align in the direction of the neural fibre bundle). Thus, DTI enables the anatomical connections between various brain areas to be obtained and visualized non-invasively, as in the "human connectome project". Optionally, the experimental data comprises Diffusion Tensor Imaging (DTI) data Electroencephalography data (EEG) is a noninvasive technique of obtaining and recording signals approximating the electrical activity of the brain, enabling the spontaneous electrical activity of the brain over a period of time to be recorded. EEG has a high temporal resolution and is often effectively used to characterize epilepsy, for example. Optionally, the experimental data comprises Electroencephalography data (EEG) data Magnetoencephalography (MEG) imaging is a functional neuroimaging technique. Magnetometers are placed around the brain of a subject, to enable the magnetic response of the brain to be measured. Like EEG, it is responsive quickly in time (on the order of 10 ms), unlike fMRI which depends on changes in blood flow. Thus, MEG imaging is beneficial for accurately identifying changes in the auditory and sensor areas of a patient. Optionally, the experimental data comprises Magnetoencephalography (MEG) data.

Positron Emission Tomography (PET) involves feeding a patient, prior to imaging, with a radioligand which is metabolized within the human body. Once the patient is being scanned in the PET scanner, the radioligand emits positrons which can be detected by the PET scanner. The emission of the positrons is proportional to the metabolic rate in a given area of the patient, and thus this imaging technique is appropriate for discovering certain cancers or metabolically-linked diseases which cause a change in the metabolic rate. Optionally, the experimental data comprises Positron Emission Tomography (PET) data.

SPECT is a gamma-ray imaging modality enabling accurate localisation in 3D space. Optionally, the experimental data comprises SPECT data.

The connectome information (at least any combination of DTI, fMRI, EEG, MEG information) may be supplemented by data on receptor densities measured by PET or SPECT. The higher the detected receptor density is, the stronger does a brain area respond to binding neurotransmitters released by the connected brain areas. Receptor densities crucially determine the functional connectivity between two brain areas and can dynamically change over the course of a few days, for example.

Optionally, the experimental data comprises data from a plurality of different patients, enabling the semantic model to be extended to a comparison of several, or a large number of patients.

Optionally, the term "functional and/or structural connection" may be referred to as a "connectomic relationship".

Meta-databases, such as those of the "Human Allen Brain Atlas" or the "Brede Ontology", as discussed above, and may others, may be imported into, or referenced from, this flexible network.

The flexibility of the database enables any combination of the above input data sources may be used.

Use Cases—Clinical Perspective

It will be appreciated that, with the highly flexible model outlined above, the knowledge model thus generated can be queried from many perspectives. A medical doctor can query the knowledge model from the "patient perspective" and ask what experiments have been done for one particular patient, or which connections differ from control subjects, or what is the function of certain brain structures that have a faulty connectivity. Genomic information that was measured in specific areas of the patient may be input into the model. Alternatively, a doctor can query the model for all patients showing similar connection patterns, for means of comparison with prior cases The doctor could, for example, select individual brain structures and connections by hand in the GUI for further comparison or annotation. Alternatively, an atlas like the Brede Ontology or the Human Allen Brain Atlas can be used to annotate all connections that belong to a certain anatomical sub-system (annotating thousands of connection by hand would be time-consuming). For example, selecting "limbic lobe" from an anatomical atlas ontology would select all connections between measured Brain Structure Coordinates that are mapped to a brain structure that are in turn mapped into entries of the Ontology. Likewise, a clinician could select Brede functional ontology entries like "pleasantness" to see all relevant connections associated with that function.

Use Cases—Neurosurgery Perspective

A neurosurgeon ideally needs to know what Brain Structures can safely be removed, according to its functional or structural interconnection with the rest of the brain. A structure with high connectivity to other areas cannot be safely removed. The BioXM neurological knowledge model approach enables such interconnectivity information to be provided to a neurosurgeon in a simple report format. Additionally, available simulation tools for animating brain activity may be integrated into the knowledge model to enable a surgeon to predict the secondary effect (diachsis) of a resection, before surgery. A surgeon could use a simulation of brain plasticity integrated into the neurological knowledge model to predict how much a certain resection has potential for resection.

Use Cases—Pharmacology Perspective

An unsolved problem is how to find the right neuroactive substance to treat psychiatric patients optimally. Positive response to a drug depends on the distribution of neural receptors that a substance binds to in the brain. Patients with low receptor density for a certain drug will not respond optimally to that drug. Finding the right substance for a patient is time-consuming and can require in-patient treatment. Using the BioXM framework though, receptor densities for a patient could be measured using SPECT or PET. The data could be imported into a semantic network containing receptor information from the Human Allen Brain Atlas, and the correct compound could be found quickly.

From a different perspective, an appropriately configured knowledge model could be configured to enable new targets to be found for existing compounds. In other words, by integrating gene expression data of neural receptor proteins, and their location, the question could be asked of the semantic model "what are the functions of the Brain Structure that the receptor protein is involved in?". Alternatively, it could be possible to start with a certain disease, and query the brain structures and connections involved in the disease, to find neural receptor proteins that are predominantly localized in these brain structures, and search for existing substances that bind to this neural receptor.

Use Cases—Brain Science Perspective

A researcher may want to study the connectome to understand the interaction of different brain areas. Rather than being interested in one patient, data from tens or hundreds of patients could be loaded into the semantic model to identify functional circuits related to certain behaviours repeated frequently in the population of experimental subjects.

FIG. 13 illustrates an application of the NeuroXM (a platform of the BioXM system) to a knowledge model incorporating a DTI and an fMRI dataset for a specific patient. The NeuroXM platform has been used to display the comparison between the two aspects of the connectome in 3D space It is possible to annotate structural connections from DTI with functional connections from fMRI, or vice versa. In this way, it is possible for a user to find a connection between structural and functional connections in a patient's brain easily. Of course, importing the results of other fMRI or DTI experiments into the model can enable time-based progression comparisons to be made (if such extra data is from images of the same patient) or cohort based analyses (if the extra data originates from many different patients.

FIG. 13b) illustrates an application of the NeuroXM system to neurological gene discovery. The platform has been used to associate a connectome strength with gene expression values of a specific gene from the "Human Allen Brain Atlas". The knowledge model also comprises a brain atlas, meaning that the clinical name of the brain region of a gene expression location of interest can be viewed when the receptor location is highlighted in the GUI.

According to a second aspect, an apparatus 400 for processing neurological data is provided. The apparatus comprises:
- a data input module 402;
- an object data processing module 404;
- a relationship data processing module 406;
- an annotation data processing module 408; and a data output module 410.

The object data processing module is configured to acquire first element data and second element data representing, respectively, attributes of a first location and a second location of a subject vertebrate brain.

The relationship data processing module is configured to acquire neural connectivity data linking the first element data and the second element data, wherein the neural connectivity data comprises a representation of a functional and/or structural connection between the first region and the second region of the subject vertebrate brain, and wherein the first element data, second element data, and the neural connectivity data form a semantic network.

The annotation data processing module is configured to acquire annotation data comprising object data, and to map the annotation data to the neural connectivity data to thus generate neurological knowledge model data related to the subject vertebrate brain, wherein the neurological knowledge model data is a semantic network capable of being queried using a formal linguistic specification, wherein the formal linguistic specification is derived from the semantic network.

The data output module is configured to output the neurological knowledge model data.

Figure 14:
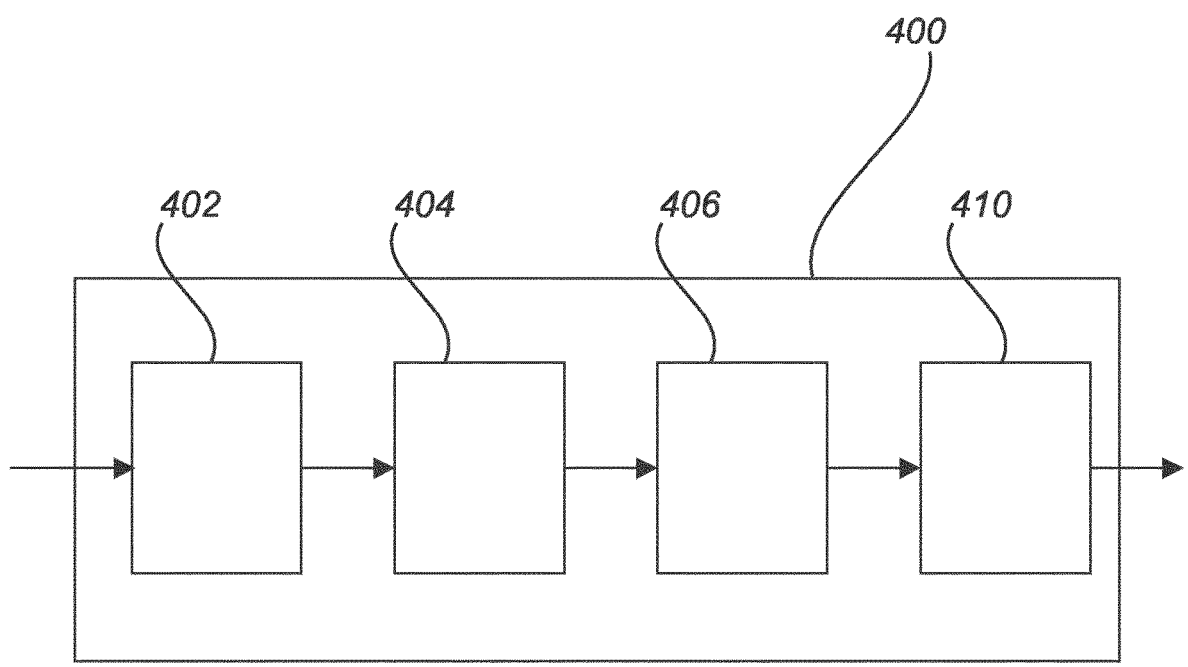
FIG. 14 illustrates an apparatus according to the second aspect.

FIG. 14 illustrates an apparatus according to the second aspect. The apparatus may be implemented, for example, in a computer apparatus, or as part of a client-server arrangement as discussed previously in this specification.

According to a third aspect, there is provided a computer program element comprising instructions which, when executed by a computer, enables the computer to carry out the method of the first aspect or its embodiments.

According to a fourth aspect, there is provided a computer program product, tangibly embodied on a carrier medium, comprising software code for carrying out the method of the first aspect.

According to the fifth aspect, there is provided a computer program product, tangibly embodied on a carrier medium, comprising a data structure containing a neurological knowledge model generated according to the method of the first aspect.

What is claimed is:

1. A method comprising
   using neuroimaging data obtained from neuroimaging of brain tissue from a subject-vertebrate brain, determining extents of neural connections between different locations in said brain,
   wherein determining said extents of said neural connections comprises causing a computer to estimate a correlation of a neural connection between brain tissues at first and second brain locations in said subject-vertebrate brain,
   wherein causing said computer to estimate said correlation between said neural connection between said brain tissues at said first and second brain locations comprises:
   receiving said neuroimaging data, said neuroimaging data being a result of having non-invasively imaged said brain tissue from said subject-vertebrate brain using a neuroimaging procedure selected from the group consisting of functional magnetic resonance imaging, diffusion tensor imaging, magnetoencephalographic imaging, positron emission tomography, single photon emission computed tomography, and electroencephalography, said neuroimaging data comprising voxels that provide information concerning a neural relationship selected from the group consisting of a neural relationship that arises from existence of a physical fiber bundle of fibers extending between said first and second brain tissues and existence of a functional association in time between said first and second brain tissues,
   from said neuroimaging data, acquiring first element data and second element data representing, respectively, attributes of said first location and said second location in said subject-vertebrate brain;
   acquiring neural connectivity data linking the first element data and the second element data, wherein the neural connectivity data comprises a representation of an extent of a functional and/or structural connection between the first location and the second location in the subject-vertebrate brain and wherein the first element data, second element data, and the neural connectivity data form a semantic network that incorporates information concerning strengths of axonal connections between tissues in said brain;
   acquiring anatomical brain atlas data;
   using the anatomical brain atlas data to annotate the neural connectivity data to thus generate neurological knowledge model data related to the subject-vertebrate brain, wherein the neurological knowledge model data is a computer implemented semantic network implemented using a database that is capable of being queried using a formal linguistic specification that is derived from the semantic network; and
   outputting the neurological knowledge model data.

2. The method of claim 1, wherein the first element data, the second element data, and the neural connectivity data each comprise a type data field.

3. The method of claim 1, wherein the neural connectivity data comprises a neural connectivity source data field and a neural connectivity target field for enabling the association of the neural connectivity data with a plurality of sets of element data and wherein the neural connectivity data further comprises neural connectivity class data defining an allowed set of relation configurations between the sets of element data in the plurality of sets of element data.

4. The method of claim 1, wherein the element data is experimental data.

5. The method according to claim 4, wherein the experimental data comprises data from a plurality of different patients.

6. The method according to claim 4, further comprising: acquiring, as the first element data, a brain structure coordinate defining a point in 3D space at which the experimental data has been acquired.

7. The method of claim 1, further comprising: acquiring, as the first element data, brain parcellation data defining a brain region in 3D space at which the experimental data has been acquired.

8. The method of claim 1, further comprising using additional data to annotate the neural connectivity data, wherein the additional data is selected from the group consisting of: a gene expression atlas of a vertebrate brain ontology, ontological brain atlas data, and a functional neurological model of a vertebrate brain.

9. The method of claim 1, further comprising: acquiring query data encoding linguistic descriptors of primitives in the element data from a user; mapping the query data onto one or more items of element data in the neurological knowledge model; and generating query result data based on the mapping of the query data onto one or more items of element data in the neurological knowledge model data using the formal linguistic specification derived from the semantic network.

10. Method of claim 9, further comprising outputting the query result data.

11. The method of claim 1, wherein the first element data, the second element data, and the neural connectivity data are each dynamically typed.

12. A non-transitory computer-readable medium having encoded therein instructions for causing a computer to carry out the steps of
using neuroimaging data obtained from neuroimaging of brain tissue from a subject-vertebrate brain, determining extents of neural connections between different locations in said brain, wherein determining said extents of said neural connections comprises
estimating a correlation of a neural connection between brain tissues at first and second brain locations in said subject-vertebrate brain, wherein estimating said correlation between said neural connection between said brain tissues at said first and second brain locations comprises:
receiving said neuroimaging data, said neuroimaging data being a result of having non-invasively imaged said brain tissue from said subject-vertebrate brain using a neuroimaging procedure selected from the group consisting of functional magnetic resonance imaging, diffusion tensor imaging, magnetoencephalographic imaging, positron emission tomography, single photon emission computed tomography, and electroencephalography,
said neuroimaging data comprising voxels that provide information concerning a neural relationship selected from the group consisting of a neural relationship that arises from existence of a physical fiber bundle of fibers extending between said first and second brain tissues and existence of a functional association in time between said first and second brain tissues, from said neuroimaging data, acquiring first element data and second element data representing, respectively, attributes of said first location and said second location in said subject-vertebrate brain;
acquiring neural connectivity data linking the first element data and the second element data, wherein the neural connectivity data comprises a representation of an extent of a functional and/or structural connection between the first location and the second location in the subject-vertebrate brain and wherein the first element data, second element data, and the neural connectivity data form a semantic network that incorporates information concerning strengths of axonal connections between tissues in said brain;
acquiring anatomical brain atlas data;
using the anatomical brain atlas data to annotate the neural connectivity data to thus generate neurological knowledge model data related to the subject-vertebrate brain, wherein the neurological knowledge model data is a computer implemented semantic network implemented using a database that is capable of being queried using a formal linguistic specification that is derived from the semantic network; and
outputting the neurological knowledge model data.

13. A computer-implemented client-side neurological data processing method comprising:
receiving neurological query data from a user and
transmitting the neurological query data to a server-side neurological data processor,
wherein the server-side neurological data processor comprises neurological knowledge model data;
receiving query result data from the server-side neurological data processor; and
displaying the query result data to a user,
the neurological model data at the server-side neurological data processor having been generated by executing a method that comprises
using neuroimaging data obtained from neuroimaging of brain tissue from a subject-vertebrate brain, determining extents of neural connections between different locations in said brain,
wherein determining said extents of said neural connections comprises causing a computer to estimate a correlation of a neural connection between brain tissues at first and second brain locations in said subject-vertebrate brain by:
receiving said neuroimaging data, said neuroimaging data being a result of having non-invasively imaged said brain tissue from said subject-vertebrate brain using a neuroimaging procedure selected from the group consisting of functional magnetic resonance imaging, diffusion tensor imaging, magnetoencephalographic imaging, positron emission tomography, single photon emission computed tomography, and electroencephalography, said neuroimaging data comprising voxels that provide information concerning a neural relationship selected from the group consisting of a neural relationship that arises from existence of a physical fiber bundle of fibers extending between said first and second brain tissues and existence of a functional association in time between said first and second brain tissues,
from said neuroimaging data, acquiring first element data and second element data representing, respectively, attributes of said first location and said second location in said subject-vertebrate brain;
acquiring neural connectivity data linking the first element data and the second element data, wherein the neural connectivity data comprises a representation of an extent of a functional and/or structural connection between the first location and the second location in the subject-vertebrate brain and wherein the first element data, second element data, and the neural connectivity data form a semantic network that incorporates information concerning strengths of axonal connections between tissues in said brain;
acquiring anatomical brain atlas data;
using the anatomical brain atlas data to annotate the neural connectivity data to thus generate the neurological knowledge model data related to the subject-vertebrate brain, wherein the neurological knowledge model data is a computer implemented semantic network implemented using a database that is capable of being queried using a formal linguistic specification that is derived from the semantic network; and outputting the neurological knowledge model data.

14. A computer-implemented server-side neurological data processing method comprising:

receiving neurological query data from a client-side neurological data processor;

mapping the neurological query data onto one or more items of element data in neurological knowledge model data comprised in a computer-implemented semantic network implemented using a database, the entries in the query data encoding linguistic descriptors of primitives in the element data; and generating neurological query result data based on the mapping of the query data onto one or more items of element data in the neurological knowledge model data; and transmitting the neurological query result data to the client-side neurological data processor, wherein the database that implements the computer-implemented semantic network is generated by a method that comprises using neuroimaging data obtained from neuroimaging of brain tissue from a subject-vertebrate brain, determining extents of neural connections between different locations in said brain, wherein determining said extents of said neural connections comprises causing a computer to estimate a correlation of a neural connection between brain tissues at first and second brain locations in said subject-vertebrate brain by:

receiving said neuroimaging data, said neuroimaging data being a result of having non-invasively imaged said brain tissue from said subject-vertebrate brain using a neuroimaging procedure selected from the group consisting of functional magnetic resonance imaging, diffusion tensor imaging, magnetoencephalographic imaging, positron emission tomography, single photon emission computed tomography, and electroencephalography, said neuroimaging data comprising voxels that provide information concerning a neural relationship selected from the group consisting of a neural relationship that arises from existence of a physical fiber bundle of fibers extending between said first and second brain tissues and existence of a functional association in time between said first and second brain tissues, from said neuroimaging data, acquiring first element data and second element data representing, respectively, attributes of said first location and said second location in said subject-vertebrate brain;

acquiring neural connectivity data linking the first element data and the second element data, wherein the neural connectivity data comprises a representation of an extent of a functional and/or structural connection between the first location and the second location in the subject-vertebrate brain and wherein the first element data, second element data, and the neural connectivity data form a semantic network that incorporates information concerning strengths of axonal connections between tissues in said brain;

acquiring anatomical brain atlas data;

using the anatomical brain atlas data to annotate the neural connectivity data to thus generate the neurological knowledge model data related to the subject-vertebrate brain, wherein the neurological knowledge model data is the computer implemented semantic network that is implemented using a database that is capable of being queried using a formal linguistic specification that is derived from the semantic network; and outputting the neurological knowledge model data.

* * * * *